(12) United States Patent
Verardi et al.

(10) Patent No.: US 12,029,787 B2
(45) Date of Patent: Jul. 9, 2024

(54) METHOD FOR GENERATING RECOMBINANT POXVIRUSES

(71) Applicant: University of Connecticut, Farmington, CT (US)

(72) Inventors: Paulo H. Verardi, Mansfield, CT (US); Brittany Jasperse, Brick, NJ (US); Caitlin M. O'Connell, Glastonbury, CT (US); Yuxiang Wang, Storrs, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 172 days.

(21) Appl. No.: 17/365,746

(22) Filed: Jul. 1, 2021

(65) Prior Publication Data

US 2022/0072122 A1 Mar. 10, 2022

Related U.S. Application Data

(60) Provisional application No. 63/046,761, filed on Jul. 1, 2020.

(51) Int. Cl.
| | | |
|---|---|---|
| A61K 45/06 | (2006.01) | |
| A61K 39/275 | (2006.01) | |
| C12N 7/00 | (2006.01) | |
| C12N 15/86 | (2006.01) | |

(52) U.S. Cl.
CPC .......... *A61K 39/275* (2013.01); *A61K 45/06* (2013.01); *C12N 7/00* (2013.01); *C12N 15/86* (2013.01); *C12N 2710/24034* (2013.01); *C12N 2710/24041* (2013.01); *C12N 2710/24051* (2013.01)

(58) Field of Classification Search
None
See application file for complete search history.

(56) References Cited

U.S. PATENT DOCUMENTS

| 7,094,412 B2 | 8/2006 | Howley et al. |
| 8,753,648 B2 | 6/2014 | Falkner et al. |
| 2014/0377870 A1 | 12/2014 | Jacobs et al. |

OTHER PUBLICATIONS

Aguilar, J. et al.; "Vaccine adjuvants revisited"; Vaccine, vol. 25, Issue No. 19; pp. 3752-3762 (2007).
Cao, J. et al.; "gpt-gus fusion gene for selection and marker in recombinant poxviruses"; Biotechniques, vol. 22, Issue No. 2; 1997; pp. 276-278.
Chakrabarti, S. et al.; "Compact, synthetic, vaccinia virus early/late promoter for protein expression"; Biotechniques, vol. 23, Issue No. 6; 1997; pp. 1094-1097.
Doglio, L. et al.; "The Vaccinia virus E8R gene product: a viral membrane protein that is made early in infection and packaged into the virions' core"; Journal of Virology, vol. 76, Issue No. 19; 2002; pp. 9773-9786.
Drexler, I. et al.; "Highly attenuated modified vaccinia virus Ankara replicates in baby hamster kidney cells, a potential host for virus propagation, but not in various human transformed and primary cells"; Journal of General Virology, vol. 79, Part 2; 1998; pp. 347-352.
Falkner, F. et al.; "*Escherichia coli* gpt gene provides dominant selection for vaccinia virus open reading frame expression vectors"; Journal of Virology, vol. 62, Issue No. 6; 1988; pp. 1849-1854.
Falkner, F. et al.; "Transient dominant selection of recombinant vaccinia viruses"; Journal of Virology, vol. 64, Issue No. 6; 1990; pp. 3108-3111.
Gatti-Lafranconi, P. et al.; "A single mutation in the core domain of the lac repressor reduces leakiness"; Microbial Cell Factories, vol. 12, Issue No. 67; 1983; 10 pages.
Grigg, P. et al.; "Safety mechanism assisted by the repressor of tetracycline (SMART) vaccinia virus vectors for vaccines and therapeutics"; PNAS USA, vol. 110, Issue No. 38; 2013; pp. 15407-15412.
Hagen, C. et al.; "Antibiotic-dependent expression of early transcription factor subunits leads to stringent control of vaccinia virus replication"; Virus research, vol. 181; 2014; pp. 43-52.
Hatch, G. et al.; "Assessment of the protective effect of Imvamune and Acam2000 vaccines against aerosolized monkeypox virus in cynomolgus macaques"; Journal of Virology, vol. 87, Issue No. 14; 2013; pp. 7805-7815.
Hayasaka, D. et al.; "Pathogeneses of respiratory infections with virulent and attenuated vaccinia viruses"; Virology Journal, vol. 4, Article No. 22; 2007; DOI: 10.1186/1743-422X-4-22.
Hughes, C. et al.; "Vaccinia virus infections in martial arts gym, Maryland, USA 2008"; Emerging Infectious Diseases, vol. 17, Issue No. 4; 2011; pp. 730-733.
Jasperse, B. et al.; "EPPIC (Efficient Purification by Parental Inducer Constraint) Platform for Rapid Generation of Recombinant Vaccinia Viruses"; Molecular Therapy Methods and Clinical Development, vol. 17; 2020; pp. 731-738.
Jesus, D.M., et al.; "Vaccinia virus protein A3 is required for the production of normal immature virions and for the encapsidation of the nucleocapsid protein L4"; Virology, vol. 481; 2015; pp. 1-12.
Kato, S. et al.; "Temperature-sensitive mutants in the vaccinia virus 4b virion structural protein assemble malformed, transcriptionally inactive intracellular mature virions"; Virology, vol. 330, Issue No. 1; 2004; pp. 127-146.
Kato, S. et al.; "The vaccinia virus E8R gene product is required for formation of transcriptionally active virions"; Virology, vol. 367, Issue No. 2; 2007; pp. 398-412.
Lederman, E. et al.; "Progressive vaccinia: case description and laboratory-guided therapy with vaccinia immune globulin, ST-246, and CMX001"; Journal of Infectious Diseases, vol. 206, Issue No. 9; 2012; pp. 1372-1385.
Legrand, F. et al.; "Induction of potent humoral and cell mediated immune responses by attenuated vaccinia virus vectors with deleted serpin genes"; Journal of Virology, vol. 78, Issue No. 6; 2004; pp. 2770-2779.

(Continued)

*Primary Examiner* — Nicole Kinsey White
(74) *Attorney, Agent, or Firm* — CANTOR COLBURN LLP

(57) ABSTRACT

Disclosed herein are methods for the rapid generation of recombinant poxviruses, for example, to enable vaccine development.

9 Claims, 14 Drawing Sheets

Specification includes a Sequence Listing.

(56) References Cited

OTHER PUBLICATIONS

Lindholm, D. et al.; "Preemptive Tecovirimat Use in an Active Duty Member Presenting with Acute Myeloid eukemia after Smallpox Vaccination"; Clinical Infectious Diseases, vol. 69, Issue No. 12; 2019; pp. 2205-2207.

Maki, J. et al.,; "Oral vaccination of wildlife using a vaccinia-rabies-glycoprotein recombinant virus vaccine (Raboral V-RG((R))): a global review" Vet Res., vol. 48, Issue No. 1; 2017; pp. 57.

Marcinak, J. et al.; "Household transmission of vaccinia virus from contact with a military smallpox vaccinee—Illinois and Indiana, 2007"; Morbidity and Mortality Weekly Report, vol. 56, Issue No. 9; 2007; pp. 478-481.

Meng, X. et al. "Vaccinia virus A6L encodes a virion core protein required for formation of mature virion"; Journal of Virology, vol. 81, Issue No. 3; 2007; pp. 1433-1443.

Meng, X. et al.; "Vaccinia virus A6 is essential for virion membrane biogenesis and localization of virion membrane proteins to sites of virion assembly"; Journal of Virology, vol. 86, Issue No. 10; 2012; pp. 5603-5613.

Moss, B.; "Genetically engineered poxviruses for recombinant gene expression, vaccination, and safety"; PNAS USA, vol. 93, Issue No. 21; 1996; pp. 11341-48.

O'Connell, C. et al.; "Replication-inducible vaccinia virus vectors with enhanced safety in vivo"; PLoS One, vol. 15; 2020; DOI: https://doi.org/10.1371/journal.pone.

Sadler, J. et al.; "A perfectly symmetric lac operator binds the lac repressor very tightly"; PNAS USA, vol. 80; 1983; pp. 6785-6789.

Shao, H., et al. "Secondary and tertiary transmission of vaccinia virus after sexual contact with a smallpox vaccinee—San Diego, California, 2012"; Morbidity and Mortality Weekly Report, vol. 62, Issue No. 8; 2013; pp. 145-147.

Tolonen, N. et al.; "Vaccinia virus DNA replication occurs in endoplasmic reticulum-enclosed cytoplasmic mini-nuclei"; Molecular Biology of the Cell, vol. 12, Issue No. 7; 2001; pp. 2031-2046.

Upton, C. et al.; "Poxvirus orthologous clusters: toward defining the minimum essential poxvirus genome"; Journal of Virology, vol. 77, Issue No. 13; 2003; pp. 7590-7600.

Van Dam, C. et al.; "Severe postvaccinia encephalitis with acute disseminated encephalomyelitis: recovery with early Intravenous immunoglobulin, highdose steroids, and vaccinia immunoglobulin"; Clinical Infectious Diseases, vol. 48, Issue No. 4; 2009; pp. e47-e49.

Verardi, P. et al.; "A vaccinia virus renaissance: new vaccine and immunotherapeutic uses after smallpox eradication"; Human Vaccines and Immunotherapeutics, vol. 8, Issue No. 7; 2012; pp. 961-970.

Verardi, P. et al.; "Long-term sterilizing immunity to rinderpest in cattle vaccinated with a recombinant vaccinia virus expressing high levels of the fusion and hemagglutinin glycoproteins"; Journal of Virology, vol. 76, Issue No. 2; 2002; pp. 484-91.

Wu, X. et al.; "Vaccinia virus virion membrane biogenesis protein A11 associates with viral membranes in a manner that requires the expression of another membrane biogenesis protein, A6" Journal of Virology, vol. 86, Issue No. 20; 2012; pp. 11276-86.

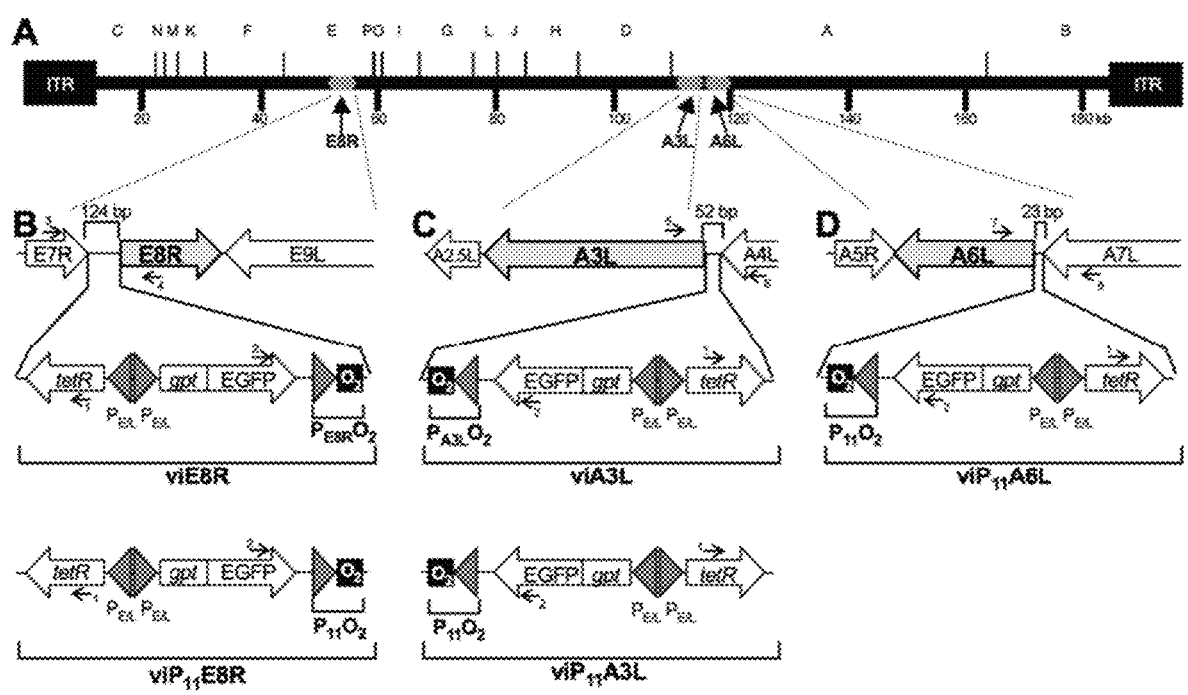
FIG. 1A-D

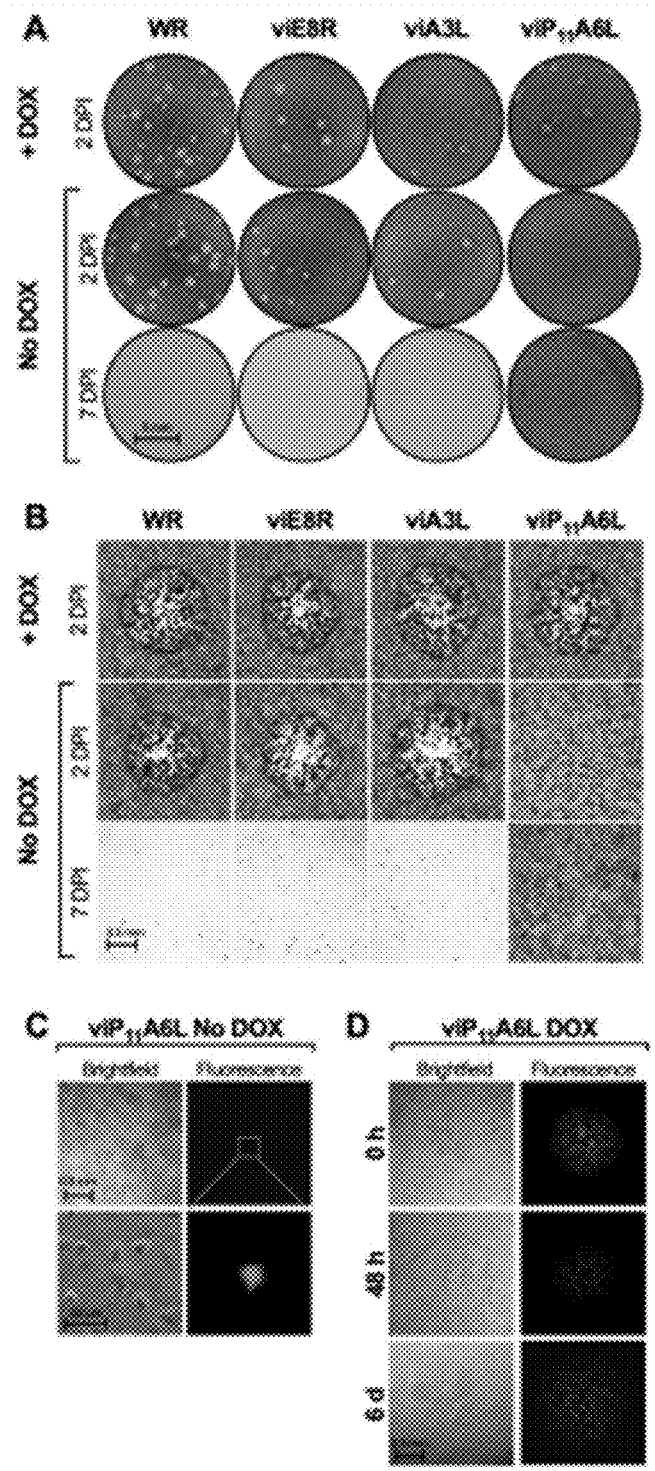
FIG. 2A-D

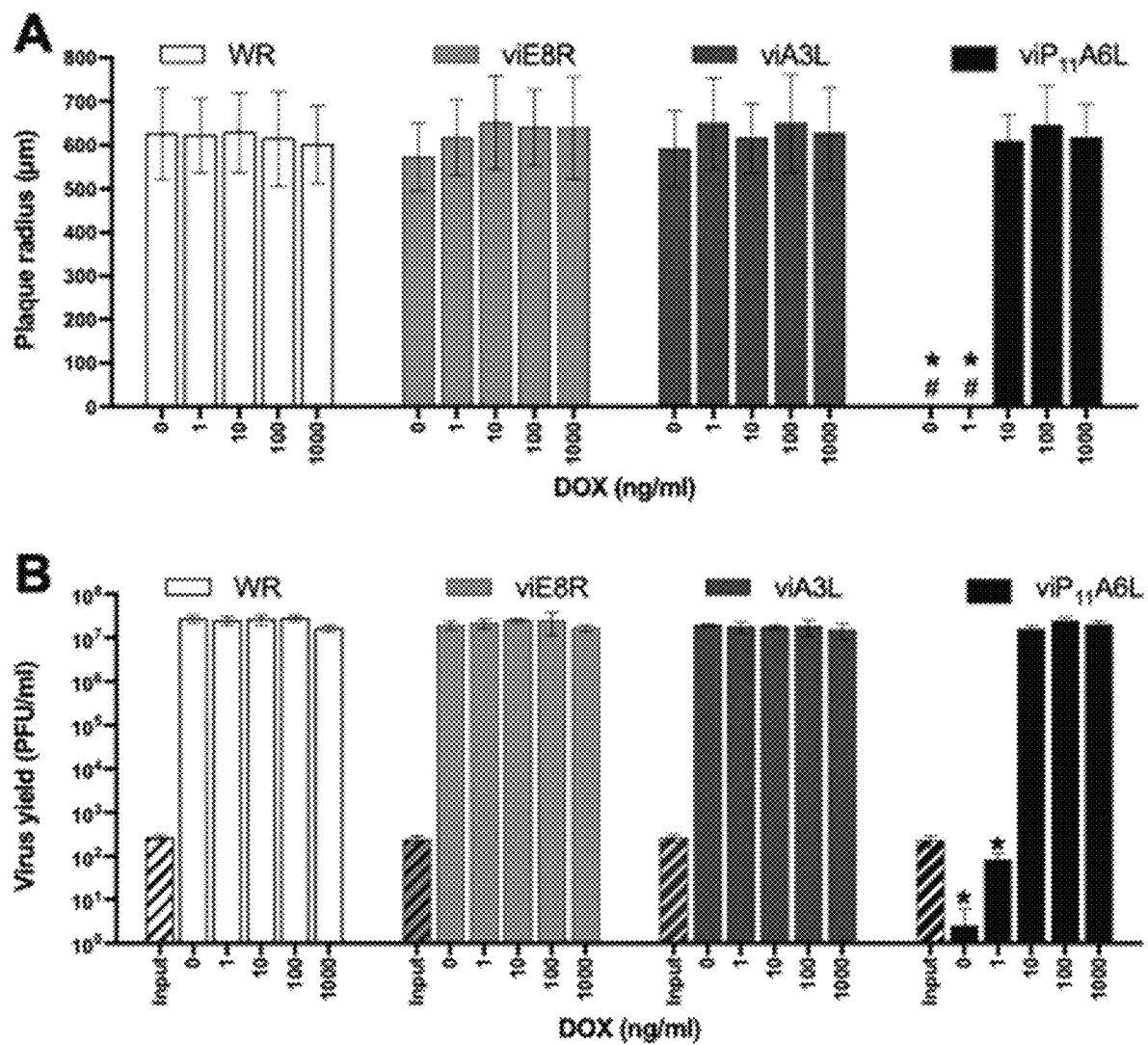
FIG. 3A-B

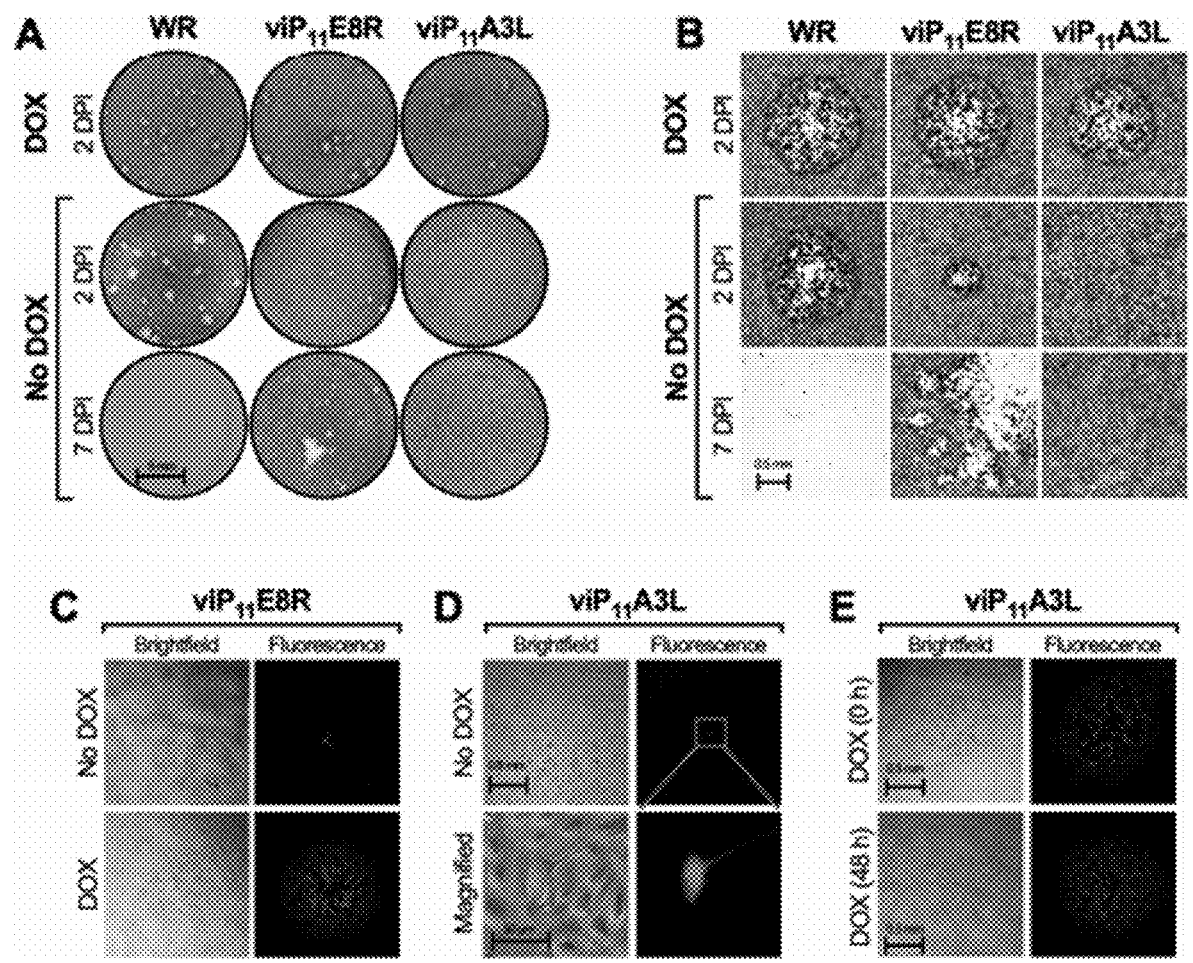
FIG. 4A-E

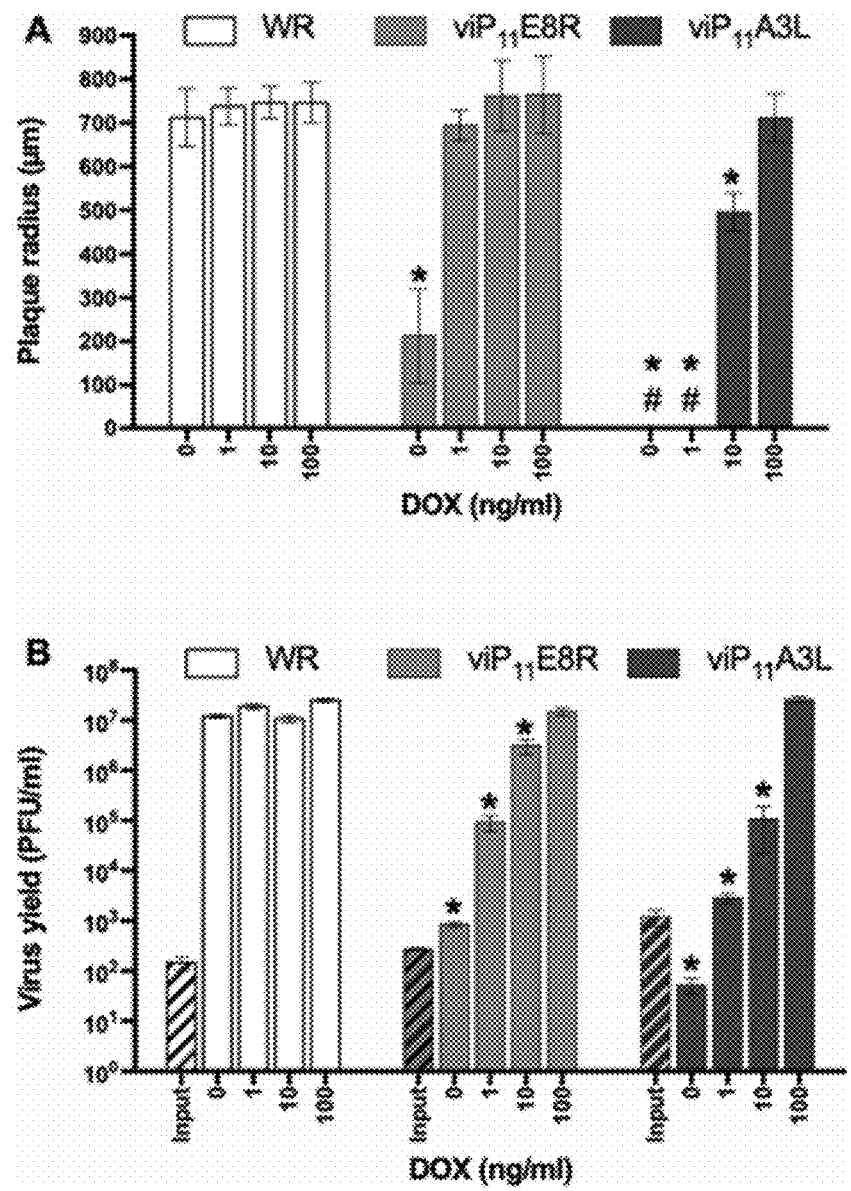
FIG. 5A-B

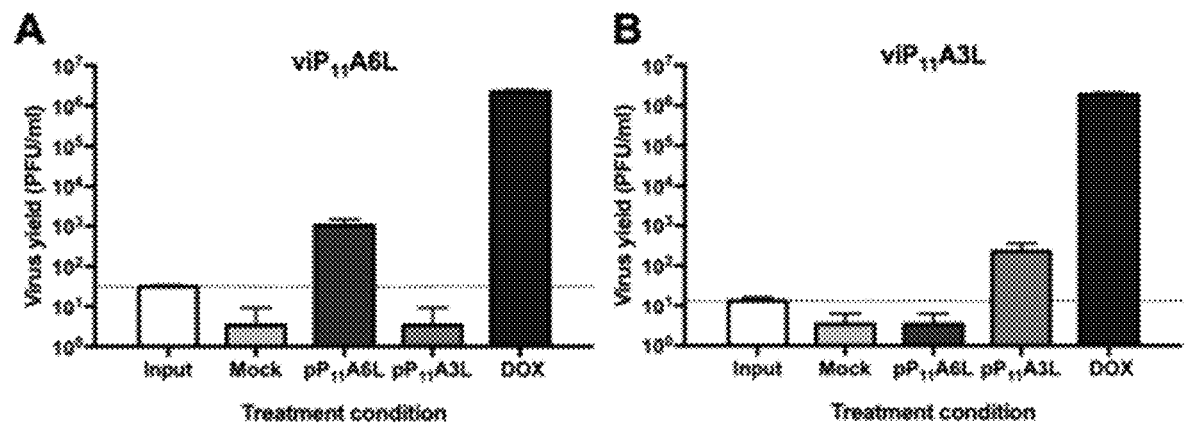
FIG. 6A-B
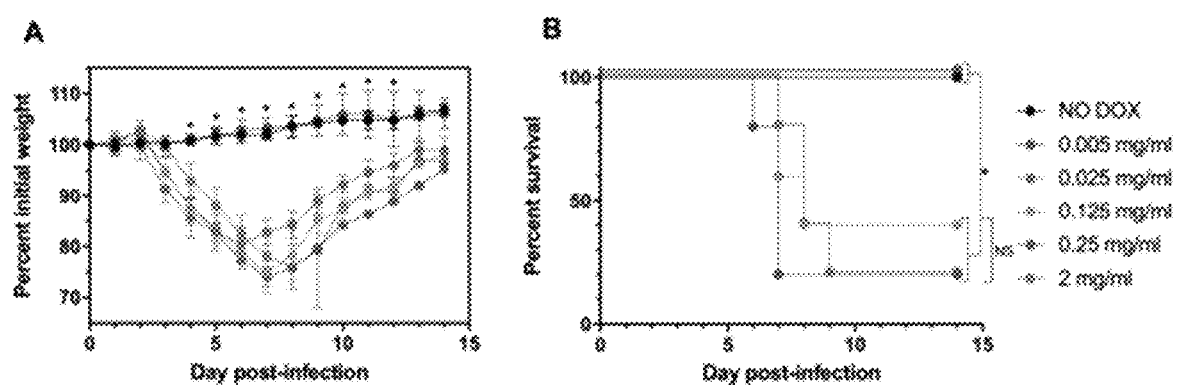
FIG. 7A-B

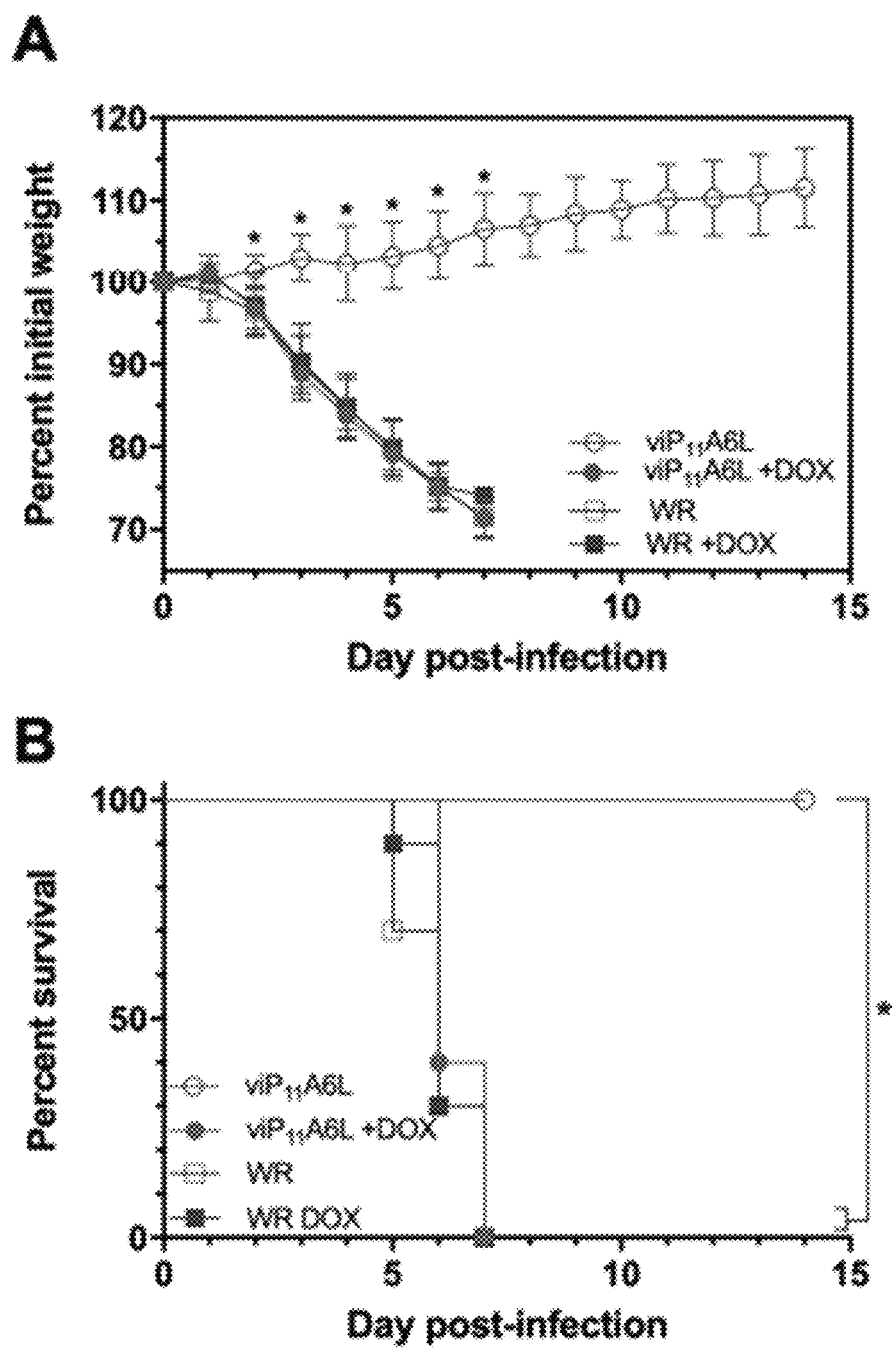
FIG. 8A-B

FIG. 10A-F

| | Parental vIND (marker / locus) | rVACV phenotype (screening marker) | rVACV Selection condition | rVACV genomic organization |
|---|---|---|---|---|
| A | Lac-inducible (DsRed / D6R) | Tet-inducible (EGFP) | DOX (no IPTG) | viTet expressing EGFP (Figure 2) |
| B | Lac-inducible (DsRed / D6R) | Tet-inducible (none) | DOX (no IPTG) | viTet expressing Zika virus Envelope |
| C | Tet-inducible (LacZ / D6R) | Lac-inducible (EGFP) | IPTG (no DOX) | viLac expressing EGFP |
| D | Tet-inducible (EGFP / D6R) | Constitutive (none*) | NONE | VACV expressing GOI (DsRed) (Figure 5) |
| E | Tet-inducible (EGFP / F17R) | Constitutive (DsRed) | NONE | VACV expressing cancer neoepitopes (CN) |
| F | Tet-inducible (EGFP / A6L) | Lac-inducible (DsRed) | IPTG (no DOX) | viLac expressing DsRed |
| G | Lac-inducible (DsRed / A6L) | Tet-inducible (LacZ) | DOX (no IPTG) | viTet expressing LacZ |

FIG. 16A-G

SEQUENCE LISTING

```
<160> NUMBER OF SEQ ID NOS: 25

<210> SEQ ID NO 1
<211> LENGTH: 6
<212> TYPE: PRT
<213> ORGANISM: Artificial Sequence
<220> FEATURE:
<223> OTHER INFORMATION: A/T rich region
<220> FEATURE:
<221> NAME/KEY: X
<222> LOCATION: (6)..(6)
<223> OTHER INFORMATION: A or G

<400> SEQUENCE: 1

Thr Ala Ala Ala Thr Xaa
1               5
```

<210> SEQ ID NO 2
<211> LENGTH: 6
<212> TYPE: PRT
<213> ORGANISM: Artificial Sequence
<220> FEATURE:
<223> OTHER INFORMATION: transcriptional initiator

<400> SEQUENCE: 2

Thr Ala Ala Ala Thr Ala
1               5

<210> SEQ ID NO 3
<211> LENGTH: 65
<212> TYPE: DNA
<213> ORGANISM: Artificial Sequence
<220> FEATURE:
<223> OTHER INFORMATION: promoter from table

<400> SEQUENCE: 3
atttagaata tatgtatgta aaatatagt agaatttcat tttgttttt tctatgctat      60 aaatg                                                                65

<210> SEQ ID NO 4
<211> LENGTH: 70
<212> TYPE: DNA
<213> ORGANISM: Artificial Sequence
<220> FEATURE:
<223> OTHER INFORMATION: promoter from table

<400> SEQUENCE: 4
atatagtaga atttcatttt gttttttct atgctataaa tatccctatc agtgatagag      60
acggccgatg                                                           70

<210> SEQ ID NO 5
<211> LENGTH: 127
<212> TYPE: DNA
<213> ORGANISM: Artificial Sequence
<220> FEATURE:
<223> OTHER INFORMATION: promoter from table

<400> SEQUENCE: 5
gtataatccc attctaatac tttaacctga tgtattagca tcttattaga atattaacct     60
aactaaaaga cataacataa aaactcatta catagttgat aaaaagcggt aggatataaa   120
tattatg                                                             127

<210> SEQ ID NO 6
<211> LENGTH: 150
<212> TYPE: DNA
<213> ORGANISM: Artificial Sequence
<220> FEATURE:
<223> OTHER INFORMATION: promoter from table

<400> SEQUENCE: 6
gtataatccc attctaatac tttaacctga tgtattagca tcttattaga atattaacct     60
aactaaaaga cataacataa aaactcatta catagttgat aaaaagcggt aggatataaa   120
tatccctatc agtgatagag acggccgatg                                    150

<210> SEQ ID NO 7
<211> LENGTH: 55
<212> TYPE: DNA
<213> ORGANISM: Artificial Sequence -continued

```
<220> FEATURE:
<223> OTHER INFORMATION: promoter from table

<400> SEQUENCE: 7
taagattgga tattaaaatc acgctttcga gtaaaaacta cgaatataaa taatg      55

<210> SEQ ID NO 8
<211> LENGTH: 80
<212> TYPE: DNA
<213> ORGANISM: Artificial Sequence
<220> FEATURE:
<223> OTHER INFORMATION: promoter from table

<400> SEQUENCE: 8
taagattgga tattaaaatc acgctttcga gtaaaaacta cgaatataaa tatccctatc    60
agtgatagag acggccgatg                                               80

<210> SEQ ID NO 9
<211> LENGTH: 26
<212> TYPE: DNA
<213> ORGANISM: Artificial Sequence
<220> FEATURE:
<223> OTHER INFORMATION: promoter from table

<400> SEQUENCE: 9
acaactaaat ctgtaaataa ataatg                                        26

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gacgccttag ccattgagat                                               20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
acaaccacta cctgagcacc                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tctccgcaca tggaactcat                                               20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
```

```
cagagaacga tccattagca                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gatgctactt cgtcgatgga                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
caaatccagg agcagcatct                                              20

<210> SEQ ID NO 16
<211> LENGTH: 19
<212> TYPE: DNA
<213> ORGANISM: Artificial Sequence
<220> FEATURE:
<223> OTHER INFORMATION: primer

<400> SEQUENCE: 16
tatcaacatc tgatgcgct                                               19

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
atgttattgc gtctgatgcc                                              20

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
attttccaat tccgtaggta aacga                                        25

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
tgatcatgct catgaacttc gtcta                                        25

<210> SEQ ID NO 20
<211> LENGTH: 26
<212> TYPE: DNA
<213> ORGANISM: Artificial Sequence
```

```
<220> FEATURE:
<223> OTHER INFORMATION: primer

<400> SEQUENCE: 20
taaatacggc cgatggacaa acttag                                             26

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
acgatagcta gcttagaatt tatacg                                             26

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
taaatacggc cgatggaagc cgtg                                               24

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
cataatgcta gcctaaaata gttc                                               24

<210> SEQ ID NO 24
<211> LENGTH: 7
<212> TYPE: DNA
<213> ORGANISM: Artificial Sequence
<220> FEATURE:
<223> OTHER INFORMATION: VACV early transcriptional termination sequence
<220> FEATURE:
<221> NAME/KEY: misc_feature
<222> LOCATION: (6)..(6)
<223> OTHER INFORMATION: n is a, c, g, or t

<400> SEQUENCE: 24 tttttnt                                                                   7

<210> SEQ ID NO 25
<211> LENGTH: 90
<212> TYPE: DNA
<213> ORGANISM: Artificial Sequence
<220> FEATURE:
<223> OTHER INFORMATION: back-to-back PE/L synthetic promoters

<400> SEQUENCE: 25
tatttatatt ccaaaaaaaa aaaataaaat ttcaattttt aactgcagtt aaaaattgaa         60
attttatttt ttttttttgg aatataaata                                         90
```

METHOD FOR GENERATING RECOMBINANT POXVIRUSES

CROSS-REFERENCE TO RELATED APPLICATIONS

The present application claims the benefit of U.S. Provisional Patent Application No. 63/046,761, filed on Jul. 1, 2020, which is hereby incorporated by reference herein.

STATEMENT OF GOVERNMENT SUPPORT

This invention was made with government support under Grant 2014-31100-06009 awarded by the US Department of Agriculture (USDA). The government has certain rights in the invention.

SEQUENCE LISTING

The Instant Application contains a Sequence Listing which has been submitted electronically in ASCII format and is hereby incorporated by reference in its entirety. Said ASCII copy, created on Nov. 18, 2021 is named "Sequence List TXT File UCT0285US (20-059)" and is 5,752 bytes in size.

BACKGROUND

Poxviruses such as vaccinia virus (VACV) have been widely used as vaccine and therapeutic vectors. However, methods of generating and purifying recombinant poxviruses are often time-consuming, cumbersome, and in some cases require specialized cell lines or equipment. There is an unmet need for improved methods for the rapid generation of recombinant viruses, for example, to enable vaccine development.

SUMMARY

Disclosed herein are methods for the rapid generation of recombinant viruses, for example, to enable vaccine development.

In one aspect, disclosed herein are methods for generating recombinant vaccina viruses (rVACVs) comprising homologously recombining a replication-inducible VACV (vIND) parental virus and a DNA shuttle vector to generate the rVACVs.

In some embodiments, the methods further comprise transfecting the DNA shuttle vector into parental vIND.

In some embodiments, the methods further comprise purifying the rVACVs from the parental vIND. In some such embodiments, purifying comprises a first purification step and a second purification step. For example, in some embodiments, the first purification step and the second purification step each independently comprise infecting parental VACV-infected cells with cell lysate.

In some embodiments, the recombinant rVACVs further express enhanced green fluorescence protein. In some such embodiments, the methods further comprise collecting enhanced green fluorescence protein (EGFP$^+$) plaques between the first purification step and the second purification step.

In some embodiments, the methods further comprise comprising collecting the EGFP$^+$ plaques after the second purification step to obtain purified a rVACV clone.

In some embodiments, the methods further comprise amplifying the purified rVACV clone.

In some embodiments, wherein transfecting comprises adding one or more inducers.

In some embodiments, the inducer is an rVACV inducer. In some such embodiments, the rVACV inducer is a tetracycline antibiotic. Exemplary tetracycline antibiotics include, but are not limited to, chlortetracycline, oxytetracycline, tetracycline, demethylchlortetracycline, rolitetracycline, lymecycline, clomocycline, methacycline, doxycycline, minocycline, and tertiary-butylglycylamidominocycline. In certain embodiments, the tetracycline antibiotic is doxycycline.

In some embodiments, the inducer is a parental inducer. An exemplary parental inducer is isopropyl β-D-1-thiogalactopyranoside (IPTG).

In some embodiments, the rVACVs further comprise a screening marker. Exemplary screening markers include, but are not limited to, dsRed, EGFP, gusA, and lacZ.

In some embodiments, the DNA shuttle vector comprises a promotor and a gene of interest (GOI) flanked by regions homologous to the VACV genome. In some such embodiments, the homologous regions comprise an essential gene controlled by the inducible mechanism and its upstream gene.

In some embodiments, is the vIND parental virus is a tet-inducible parental VACV. In some embodiments, the tet-inducible parental VACV expresses LacZ.

In some embodiments, the vIND parental virus is a lac-inducible parental VACV. In some such embodiments, the vIND parental virus lac-inducible expresses dsRed.

In some embodiments, the rVACVs are recombinant poxviruses. In some such embodiments, the recombinant poxvirus is selected from recombinant orthopoxvirus, recombinant parapoxvirus, recombinant yatapoxvirus, recombinant molluscipoxvirus, and recombinant avipoxviruses. Exemplary recombinant poxvirus include, but are not limited to, recombinant smallpox virus, recombinant vaccinia virus, recombinant cowpox virus, recombinant monkeypox virus, recombinant rabbitpox virus, recombinant orf virus, recombinant pseudocowpox, bovine papular stomatitis virus, recombinant tanapox virus, recombinant yaba monkey tumor virus, recombinant molluscum contagiosum virus, recombinant canarypox virus, and recombinant fowlpox virus.

In another aspect, disclosed herein are methods for generating recombinant poxviruses, comprising homologously recombining a tet-inducible parental VACV a transfer vector to generate the recombinant poxviruses. In some such embodiments, the recombinant poxvirus is selected from recombinant orthopoxvirus, recombinant parapoxvirus, recombinant yatapoxvirus, recombinant molluscipoxvirus, and recombinant avipoxviruses. Exemplary recombinant poxvirus include, but are not limited to, recombinant smallpox virus, recombinant vaccinia virus, recombinant cowpox virus, recombinant monkeypox virus, recombinant rabbitpox virus, recombinant orf virus, recombinant pseudocowpox, bovine papular stomatitis virus, recombinant tanapox virus, recombinant yaba monkey tumor virus, recombinant molluscum contagiosum virus, recombinant canarypox virus, and recombinant fowlpox virus.

In some embodiments, tet-inducible parental VACV inducibly expresses a VACV gene essential for virus replication, including but not limited to, the E8R gene, the A3L gene, the A6L gene, the D6R gene, the F17R gene, and combinations thereof.

In some embodiments, the transfer vector comprises an A/T-rich stretch of about 20 base pairs, a 6 base pair spacer region, and a highly conserved TAAAT(A/G) (SEQ ID NO:

1) transcriptional initiator element. In some such embodiments, the transcriptional initiator element is TAAATA (SEQ ID NO:2). In certain embodiments, the transfer vector is selected from SEQ ID NOs:10-22.

In some embodiments, the methods further comprise purifying the tet-inducible parental VACV. In some such embodiments, purifying comprises a first purification step and a second purification step. In certain embodiments, the first purification step and the second purification step each independently comprise infecting parental VACV-infected cells with cell lysate.

In some embodiments, the methods further comprise collecting enhanced green fluorescence protein (EGFP+) plaques between the first purification step and the second purification step.

In some embodiments, the methods further comprise comprising collecting the EGFP+ plaques after the second purification step to obtain purified a recombinant poxviruses clone.

In some embodiments, the methods further comprise amplifying the purified recombinant poxviruses clone.

In some embodiments, the methods further comprise preparing a vaccine or medicament from the purified recombinant poxviruses clone.

In another aspect, disclosed herein are vaccines and medicament comprising one or more recombinant poxviruses comprising tet operon elements or lac operon elements.

In some embodiments of the vaccines or medicaments disclosed herein, the recombinant poxvirus is selected from recombinant orthopoxvirus, recombinant parapoxvirus, recombinant yatapoxvirus, recombinant molluscipoxvirus, and recombinant avipoxviruses. Exemplary recombinant poxvirus include, but are not limited to, recombinant smallpox virus, recombinant vaccinia virus, recombinant cowpox virus, recombinant monkeypox virus, recombinant rabbitpox virus, recombinant orf virus, recombinant pseudocowpox, bovine papular stomatitis virus, recombinant tanapox virus, recombinant yaba monkey tumor virus, recombinant molluscum contagiosum virus, recombinant canarypox virus, and recombinant fowlpox virus.

In some embodiments of the vaccines and medicaments disclosed herein, the tet operon elements comprise a tet gene. In some embodiments of the vaccine and medicaments disclosed herein, the lac operon elements comprise a lac gene.

In some embodiments of the vaccines and medicaments disclosed herein, the tet gene is the tetR gene. In some embodiments of the vaccines and medicaments disclosed herein, the lac gene is the lacI gene.

In some embodiments of the vaccines and medicaments disclosed herein, the tet operon elements further comprise a tet operator element ($O_2$). In some embodiments, the lac operon elements further comprise a lac operator element (O).

In another aspect, disclosed herein are methods of inducing an immune response, comprising administering one or more recombinant poxviruses comprising tet operon elements or lac operon elements.

In some embodiments of inducing the immune response disclosed herein, the recombinant poxvirus is selected from recombinant orthopoxvirus, recombinant parapoxvirus, recombinant yatapoxvirus, recombinant molluscipoxvirus, and recombinant avipoxviruses. Exemplary recombinant poxvirus include, but are not limited to, recombinant smallpox virus, recombinant vaccinia virus, recombinant cowpox virus, recombinant monkeypox virus, recombinant rabbitpox virus, recombinant orf virus, recombinant pseudocowpox, bovine papular stomatitis virus, recombinant tanapox virus, recombinant yaba monkey tumor virus, recombinant molluscum contagiosum virus, recombinant canarypox virus, and recombinant fowlpox virus.

In some embodiments of inducing the immune response disclosed herein, the tet operon elements comprise a tet gene. In some embodiments of inducing the immune response disclosed herein, the lac operon elements comprise a lac gene.

In some embodiments of inducing the immune response disclosed herein, the tet gene is the tetR gene. In some embodiments of inducing the immune response disclosed herein, the lac gene is the lacI gene.

In some embodiments of inducing the immune response disclosed herein, the tet operon further comprises a tet operator element ($O_2$). In some embodiments of inducing the immune response disclosed herein, the lac operon further comprises a lac operator element (O).

BRIEF DESCRIPTION OF THE FIGURES

FIGS. 1A-1D shows genomic organization of the VACVs inducibly expressing the E8R, A3L, or A6L genes. FIG. 1A shows the genome of the WR strain of VACV showing HindIII restriction fragments A through P and the location of the E8R, A3L, and A6L genes. Cassettes containing the putative E8R (PE8R) or A3L (PA3L) promoters, or the P11 promoter, followed by the tet operator (02) were inserted upstream of the E8R, A3L, or A6L genes to generate the recombinant VACVs viE8R (FIG. 1), viA3L (FIG. 1C), and viP11A6L (FIG. 1D), respectively. Replacement of PE8R and PA3L promoters with P11 resulted in viP11E8R (FIG. 1i, lower panel) and viP11A3L (FIG. 1C, lower panel). The cassettes also contain the tetR gene and the gpt-EGFP fusion gene under back-to-back synthetic early/late VACV promoters (PE/L). Arrows with numbers indicate primers (Table 2) used to amplify specific genomic regions for characterization of the viruses. ITR, inverted terminal repeat.

FIG. 2A-D show that viP11A6L forms plaques only in the presence of DOX.BS-C-1 cell monolayers were infected with the indicated VACVs at approximately 5-20 PFU/well in the absence or presence of 1 µg/ml DOX and cells were stained with crystal violet 2 or 7 DPI (FIGS. 2A and 2B) or imaged by brightfield (phase) and fluorescence microscopy (FIG. 2C and FIG. 2D). FIG. 2A is an image of representative wells showing the plaque phenotypes. FIG. 2B shows representative brightfield microscopic images of stained cells showing plaques, when present. WR refers to VACV WR (parental strain). In the absence of DOX only single EGFP+ cells were observed 2 DPI for viP11A6L (FIG. 2C), and under higher magnification, EGFP expression was contained to single cells and was the only indication of infection (red inset), suggesting abortive infections. When DOX was added at the time of infection (0 h), 48 h, or 6 days after infection (FIG. 2D), plaques were visible 2 days later (2, 4, or 8 DPI, respectively). Data is representative of two separate experiments.

FIGS. 3A and 3B viP11A6L replicates indistinguishably from WR in the presence of DOX. FIG. 3A shows the effect of DOX on plaque size was examined by infecting BS-C-1 cell monolayers with the VACVs in the absence or presence of multiple concentrations of DOX. At 36 hpi, cells were stained with crystal violet and the size (radius) of approximately 20 representative isolated plaques was measured (#indicates absence of plaques). FIG. 3B shows the effect of DOX on virus replication was examined by infecting BS- C-1 cell monolayers with the indicated VACVs at an MOI of 0.01. Cells were collected immediately to determine input titer (hatched bars) or after 48 h in the absence or presence of multiple concentrations of DOX to determine virus yield (solid bars). Titers were determined on BS-C-1 cells in the presence of 1 g/ml DOX. The data shown represent the mean viral yields from triplicate samples assayed in duplicate. Error bars indicate standard deviation. An asterisk indicates statistically significant differences (p<0.05 by two-way ANOVA followed by Tukey's multiple comparisons test) between WR and the inducible viruses at a given DOX concentration. Data is representative of two separate experiments.

FIGS. 4A-E show that viP11A3L does not form plaques and causes abortive infections in the absence of DOX.BS-C-1 cell monolayers were infected with the indicated VACVs at approximately 5-20 PFU/well in the absence or presence of 1 μg/ml DOX and cells were stained with crystal violet 2 or 7 DPI (FIG. 4A and FIG. 4B) or imaged by brightfield (phase) and fluorescence microscopy (FIG. 4C, FIG. 4D, and FIG. 4E). FIG. 4A is an image of representative wells showing the plaque phenotypes. FIG. 4B is representative brightfield microscopic images of stained cells showing plaques, when present. FIG. 4C shows that in the absence of DOX smaller plaques formed 2 DPI with viP11E8R. FIG. 4D shows that in the absence of DOX, EGFP expression was contained to single viP11A3L-infected cells and was the only indication of infection. FIG. 4E shows that when DOX was added at the time of infection or 48 h after infection, plaques were visible 2 and 4 days later, respectively. Data is representative of two separate experiments.

FIGS. 5A and 5B show that viP11A3L replicates indistinguishably from wild-type VACV in the presence of DOX. FIG. 5A shows the effect of DOX on plaque size was examined by infecting BS-C-1 cell monolayers with the VACVs in the absence or presence of multiple concentrations of DOX. At 36 hpi, cells were stained with crystal violet and the size (radius) of approximately 20 representative isolated plaques was measured (#indicates absence of plaques). FIG. 5B shows the effect of DOX on virus replication was examined by infecting BS-C-1 cell monolayers with the indicated VACVs at an MOI of 0.01. Cells were collected immediately to determine input titer (hatched bars) or after 48 h in the absence or presence of multiple concentrations of DOX to determine virus yield (solid bars). Titers were determined on BS-C-1 cells in the presence of 1 μg/ml DOX. The data shown represent the mean viral yields from triplicate samples assayed in duplicate. Error bars indicate standard deviation. An asterisk indicates statistically significant differences (p<0.05 by two-way ANOVA followed by Tukey's multiple comparisons test) between WR and the inducible viruses at a given DOX concentration.

FIGS. 6A and 6B show that transient complementation allows viP11A6L and viP11A3L replication in the absence of DOX.BS-C-1 cell monolayers were infected with viP11A6L (FIG. 6A) or viP11A3L (FIG. 6B) at an MOI of 0.01 in the absence of DOX and transfected with plasmids expressing the A6L (pP11A6L) or A3L (pP11A3L) genes under the constitutive VACV P11 promoter, or no plasmid (mock). Infections were also performed in the presence of 1 μg/ml DOX (DOX). Cells were collected immediately after infection (input, dotted line) or 2 DPI. Virus yield was determined by plaque assay on BS-C-1 cells in the presence of 1 g/ml DOX. The data shown represent the mean viral yields from triplicate samples assayed in duplicate. Error bars indicate standard deviation. Data are representative of two separate experiments.

FIGS. 7A and 7B show that viP11A6L causes weight loss in mice in the presence of DOX.Groups of female CB6F1/J mice (n=5) were inoculated intranasally with approximately $5 \times 10^4$ PFU viP11A6L in the absence or presence of different concentrations of DOX in drinking water. Weight and mortality were assessed daily. Animals were euthanized if weight loss was ≥25%. FIG. 7A shows that mean group weights are displayed as a percentage of group weight on day 0. An asterisk represents statistically significant differences (p<0.01) determined using one-way ANOVA followed by Dunnett's multiple comparisons test comparing NO DOX to all other groups at each day post-infection. Error bars indicate standard deviation. FIG. 7B shows the percent survival is shown. An asterisk represents statistically significant differences (p<0.05) by log-rank (Mantel-Cox) test for differences in survival adjusted for multiple comparisons using the Bonferroni post-hoc test. NS=not significant.

FIGS. 8A and 8B viP11A6L causes weight loss and mortality similar to WR in the presence of DOX.Groups of female CB6F1/J mice (n=10) were inoculated intranasally with approximately $2 \times 10^6$ PFU viP11A6L or WR in the absence or presence of DOX. Weight and mortality were assessed daily. Animals were euthanized if weight loss was ≥25%. Mean group weights as a percentage of group weight on Day 0 (FIG. 8A), or percent survival (FIG. 8B) are shown. Asterisks indicate statistical significance (p<0.01) by one-way ANOVA followed by Sidak's multiple comparisons test (FIG. 8A), or by log-rank (Mantel-Cox) test between indicated groups adjusted for multiple comparisons using the Bonferroni post-hoc test (FIG. 8B). Error bars indicate standard deviation.

FIG. 10A shows that in the absence of IPTG, LacI binds lacO, preventing transcription of the D6R gene and virus replication. FIG. 10B shows that in the presence of IPTG, LacI binds IPTG, undergoes a conformational change and is unable to bind lacO, thus allowing transcription from the lacO-controlled $P_{D6R}$ promoter and viLacR replication. FIG. 10C shows that viLacR forms abortive infections in the absence of IPTG that can be distinguished by expression of dsRed. FIG. 10D shows that viLacR forms dsRed$^+$ plaques in the presence of IPTG. Images taken with a fluorescence microscope 2 DPI of wells infected with approximately 20 PFU. FIG. 10E shows that when BS-C-1 cell monolayers were infected with the VACVs at approximately 30 PFU/well in the absence or presence of multiple concentrations of IPTG. After 2 days, cells were stained and fixed in 0.5% crystal violet/20% ethanol and the size (radius) of approximately 30 representative plaques was measured. Asterisks represent statistical significance (p<0.05) by one-way ANOVA with Dunnett's multiple comparisons test compared to wild-type WR at 10 mM IPTG. Bars represent geometric mean and error bars represent standard deviation. Arrow indicates absence of plaques. (F) In the absence of IPTG, only single dsRed$^+$ cells were observed 2 DPI, and under high magnification, dsRed expression was contained to single cells and was the only indication of infection, suggesting abortive infections. When IPTG was added 48 h after infection, plaques were visible 2 days later (4 DPI).

FIG. 16A-G show a variety of rVACVs (with or without a screening marker) have been produced using the EPPIC platform. Examples of lac-inducible (FIG. 16A, FIG. 16B, and FIG. 16G) or tet-inducible (FIGS. 16C-F) parental vINDs (expressing the indicated screening marker) used to generate replication-constitutive (FIG. 16D and FIG. 16E) or replication-inducible (FIG. 16A-C, FIG. 16F, and FIG. 16G) rVACVs expressing the desired GOI(s). Replication-inducible rVACVs expressing the desired GOI(s) were generated by choosing the appropriate parental vINDs and purifying the rVACV in the absence of parental inducers (swapping inducers in FIGS. 16A-C, FIG. 16F, FIG. 16G, or no inducer in FIG. 16D and FIG. 16E).

DETAILED DESCRIPTION

Figure 9:
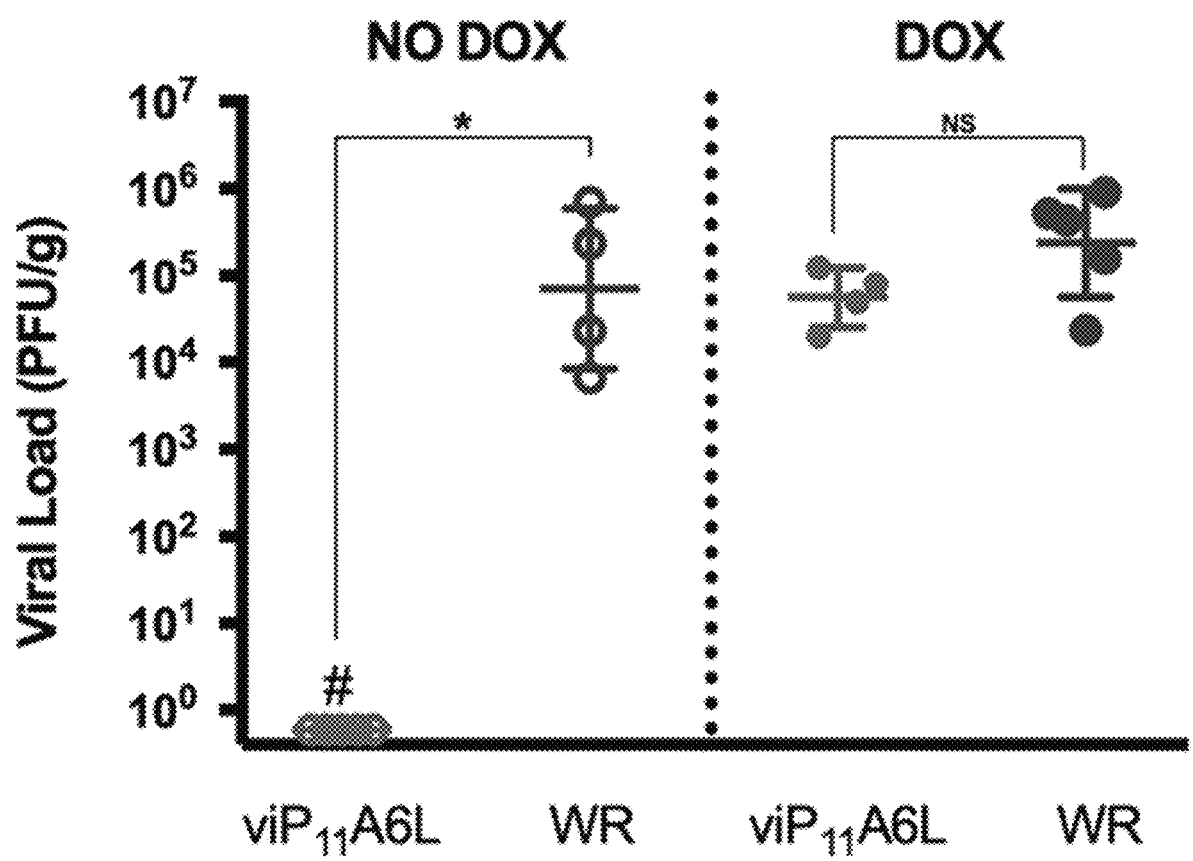
FIG. 9 shows that viP11A6L replicates indistinguishably from wild-type VACV in mice treated with DOX.Groups of five female CB6F1/J were inoculated intraperitoneally with approximately $2 \times 10^6$ PFU viP11A6L or WR in the presence or absence of DOX in drinking water. Mice were euthanized 6 DPI, and ovaries collected and processed. Ovarian homogenates were added to BS-C-1 cells in the presence of 1 μg/ml DOX to determine viral loads (#indicates absence of plaques via plaque assay). Asterisk indicates statistically significant differences (p<0.01) by Mann-Whitney test between groups in each DOX treatment. NS=not significant.

Vaccinia virus (VACV) was successfully used as a vaccine in the smallpox eradication campaign. Since then, it has been widely used in the development of vaccine and therapeutic vectors. However, methods of generating and purifying recombinant VACVs (rVACVs) are often time-consuming, cumbersome, and in some cases require specialized cell lines or equipment.

Disclosed herein is an Efficient Purification by Parental Inducer Constraint (EPPIC) platform for the rapid generation of rVACVs using a replication-inducible VACV (vIND) as a parental virus for homologous recombination. Purification of the rVACV from the parental vIND is achieved by two serial passages in the absence of inducer (i.e., parental inducer "constraint") in standard laboratory cell lines, without the need for specialized equipment, within one week.

Also disclosed herein are optimal conditions for homologous recombination and serial purification and generated a suite of vIND parental viruses to facilitate customization of the platform. Importantly, the EPPIC platform can be adapted to rapidly generate replication-deficient and replication-competent rVACVs expressing vaccine or therapeutic antigens, with or without screening markers, by simple modifications to a DNA shuttle vector, thus allowing the rapid development, updating, and refinement of personalized or custom vaccines and therapeutic vectors in a matter of days.

Definitions

Throughout the present specification and the accompanying claims, the words "comprise," "include," and "have" and variations thereof such as "comprises," "comprising," "includes," "including," "has," and "having" are to be interpreted inclusively. That is, these words are intended to convey the possible inclusion of other elements or integers not specifically recited, where the context allows. No language in the specification should be construed as indicating any non-claimed element essential to the practice of the invention.

The terms "a," "an," and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximately") one particular value, and/or to "about" (or "approximately") another particular value. When such a range is expressed, another embodiment includes from the one particular value and/or to the other particular value. Similarly, when values are expressed as approximations, by use of the antecedent "about" or "approximately" it will be understood that the particular value forms another embodiment. It will be further understood that the endpoints of each of the ranges are disclosed both in relation to the other endpoint, and independently of the other endpoint.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e.g., "such as") provided herein is intended merely to better illuminate the invention and does not pose a limitation on the scope of the invention otherwise claimed.

Units, prefixes, and symbols are denoted in their Systeme International de Unites (SI) accepted form. Unless otherwise indicated, nucleic acids are written left to right in 5' to 3' orientation; amino acid sequences are written left to right in amino to carboxy orientation.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

As used herein, the term "about" refers to a range of values of plus or minus 10% of a specified value. For example, the phrase "about 200" includes plus or minus 10% of 200, or from 180 to 220, unless clearly contradicted by context.

As used herein, the term "administering" means the actual physical introduction of a composition into or onto (as appropriate) a host or cell. Any and all methods of introducing the composition into the host or cell are contemplated according to the invention; the method is not dependent on any particular means of introduction and is not to be so construed. Means of introduction are well-known to those skilled in the art, and also are exemplified herein.

The term "immune response" refers to a reaction of the immune system to an antigenic molecule in the body of a host, which includes generation of an antigen-specific antibody and/or cellular response including a cytotoxic immune response. More specifically, an "immune response" to an antigen or vaccine composition is the development of a humoral and/or a cell-mediated immune response. For purposes of the present invention, a "humoral immune response" is an antibody-mediated immune response and involves the generation of antibodies with affinity for the antigen/vaccine of the invention, while a "cell-mediated immune response" is one mediated by T-lymphocytes and/or other white blood cells. A "cell-mediated immune response" is elicited by the presentation of antigenic epitopes in association with Class I or Class II molecules of the major histocompatibility complex (MHC). A "cell-mediated immune response" also refers to the production of cytokines, chemokines and other such molecules produced by activated T-cells and/or other white blood cells, including those derived from CD4+ and CD8+ T-cells.

The "immune response" can preferably be a "protective" immune response, however it is not necessary that the immune response is protective, since it may also be beneficial if the spread of an infectious disease is decreased or blocked in a population. A "protective" immune response refers to the ability of a vaccine to elicit an immune response, either humoral or cell mediated or both, which serves to protect the mammal from an infection. The protection provided need not be absolute, i.e., the infection need not be totally prevented or eradicated, if there is a statistically significant improvement compared with a control population of mammals. Protection may be limited to mitigating the severity or rapidity of onset of symptoms of the infection.

The terms "modulate," "modulation," or "modulating" are art-recognized and refer to up-regulation (i.e., activation, stimulation, increase), or down-regulation (i.e., inhibition, suppression, reduction, or decrease) of a response, or the two in combination or apart.

As used herein, "optional" or "optionally" means that the subsequently described event or circumstance may or may not occur, and that the description includes instances where said event or circumstance occurs and instances where it does not.

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a federal or state government or listed in the U.S. Pharmacopeia or other generally recognized pharmacopeia for use in animals, and more particularly in humans.

The term "poxvirus" as used in the present application refers to poxviruses of the subfamily Chordopoxyirinae (vertebrate poxviruses) (Fields Virology/eds.: Fields, B. N., Knipe, D. M., Howley, P. M.; 3rd ed, see in particular chapter 83). The terms "Examples of poxviruses" include those belonging to the genera Orthopoxvirus, Parapoxvirus, Avipoxvirus, Capripoxvirus, Lepripoxvirus, Suipoxvirus, Molluscipoxvirus and Yatapoxvirus. Most preferred are poxviruses belonging to the genera Orthopoxvirus and Avipoxvirus.

A "virus vector" or "viral vector" refers to a viral particle having infectivity, which is also a carrier for introducing a gene into a cell. A "poxvirus vector" for purposes of the present invention may be recombinant naked viral DNA or the naked viral DNA encapsulated by viral envelope proteins. The poxvirus vector may be a part of or all of the viral genome.

Generally, a "recombinant" poxvirus as described herein refers to poxviruses that are produced by standard genetic engineering methods, i.e., poxviruses of the present invention are thus genetically engineered or genetically modified poxviruses. The term "recombinant poxvirus" or thus includes poxviruses or modified vaccinia viruses which have stably integrated recombinant nucleic acid, preferably in the form of a transcriptional unit, in their genome. A transcriptional unit may include a promoter, enhancer, terminator and/or silencer. Recombinant poxviruses of the present invention may express heterologous polypeptides or proteins (antigens) upon induction of the regulatory elements.

As used herein, the terms "treat," "treating," and "treatment" include inhibiting the pathological condition, disorder, or disease, e.g., arresting or reducing the development of the pathological condition, disorder, or disease or its clinical symptoms; or relieving the pathological condition, disorder, or disease, e.g., causing regression of the pathological condition, disorder, or disease or its clinical symptoms. These terms also encompass therapy and cure. Treatment means any way the symptoms of a pathological condition, disorder, or disease are ameliorated or otherwise beneficially altered. Preferably, the subject in need of such treatment is a mammal, preferably a human.

Methods of Generating and Purifying Recombinant VACVs

Traditional methods of generating and purifying recombinant VACVs (replication-inducible or otherwise) are time-consuming (requiring many rounds of purification) and laborious (typically utilizing selection media, agarose overlay, special equipment or specialized cell lines), and often require inclusion of screening and/or selection markers in the final vector. Transient dominant selection has been used to generate marker-free recombinant VACVs, but requires repeated passage in the presence of selection media followed by passage in the absence of selection media and extensive screening, and can take months. A more recent method utilizes the antibiotic coumermycin to selectively remove coumermycin-sensitive parental VACVs from recombinant VACVs using minimal rounds of plaque purification. Other recent methods of recombinant VACV purification utilize fluorescence-activated cell sorting (FACS) to sort recombinant VACVs by either differential fluorescent marker expression or a selectable and excisable marker. While these methods enable the generation of marker-free recombinant VACVs in as little as 10 days, they require special cell lines (to excise the marker) and FACS equipment, which may not be feasible for all researchers due to biosafety restrictions on sorting risk group 2 infectious viruses.

In contrast, the EPPIC platform can be adapted to rapidly generate replication-deficient and replication-competent VACVs and other poxviruses expressing vaccine or therapeutic antigens, with or without screening markers, by simple modifications to a DNA shuttle vector, thus allowing the rapid development, updating, and refinement of personalized or custom vaccines, therapeutic vectors, and vaccines for novel pathogenic agents of pandemic potential in a matter of days.

Accordingly, disclosed herein is a novel Efficient Purification by Parental Inducer Constraint (EPPIC) platform for the rapid generation of rVACVs using a replication-inducible VACV (vIND) as a parental virus for homologous recombination. Purification of the rVACV from the parental vIND is achieved by two serial passages in the absence of inducer (i.e., parental inducer "constraint") in standard laboratory cell lines, without the need for specialized equipment, within one week.

The disclosed EPPIC platform uses standard cell lines, standard cell culture media (no agarose overlay), and minimal equipment (fluorescence and/or light microscope). In some embodiments, the disclosed EPPIC platform allows for the generation and purification of replication-competent or replication-inducible VACV vectors, with or without screening markers, by simple modifications to the DNA shuttle vector. In some embodiments, the disclosed EPPIC platform enables the rapid development, updating, and/or refinement of personalized or custom vaccines and therapeutic vectors in a matter of days. In preferred embodiments, recombinant VACVs can be purified from the parental virus within one week by simple withdrawal of inducer (i.e., inducer constraint) during serial purification.

As disclosed herein, the EPPIC platform is entirely customizable, allowing for the generation and purification of replication-competent, tet-inducible, or lac-inducible rVACVs, with or without screening markers using the purification workflow described above. To facilitate customization, this disclosure describes development of a suite of viLac and viTet parental VACVs that contain the inducible mechanism at different loci within the VACV genome (e.g. D6R, A6L, F17R) with various markers (e.g., DsRed, EGFP, gusA, or lacZ). For example, to generate a lac-inducible rVACV expressing EGFP, a tet-inducible parental VACV expressing LacZ could be used and purification performed in the absence of DOX and presence of IPTG. Conversely, to generate a tet-inducible rVACV expressing LacZ, a lac-inducible parental VACV expressing dsRed can be used and purification can be performed in the absence of IPTG and presence of DOX. In this manner, one can simply and rapidly shuffle back and forth between viLac and viTet vectors by strategic selection of the parental virus and swapping inducer constraint during purification.

Figure 14:
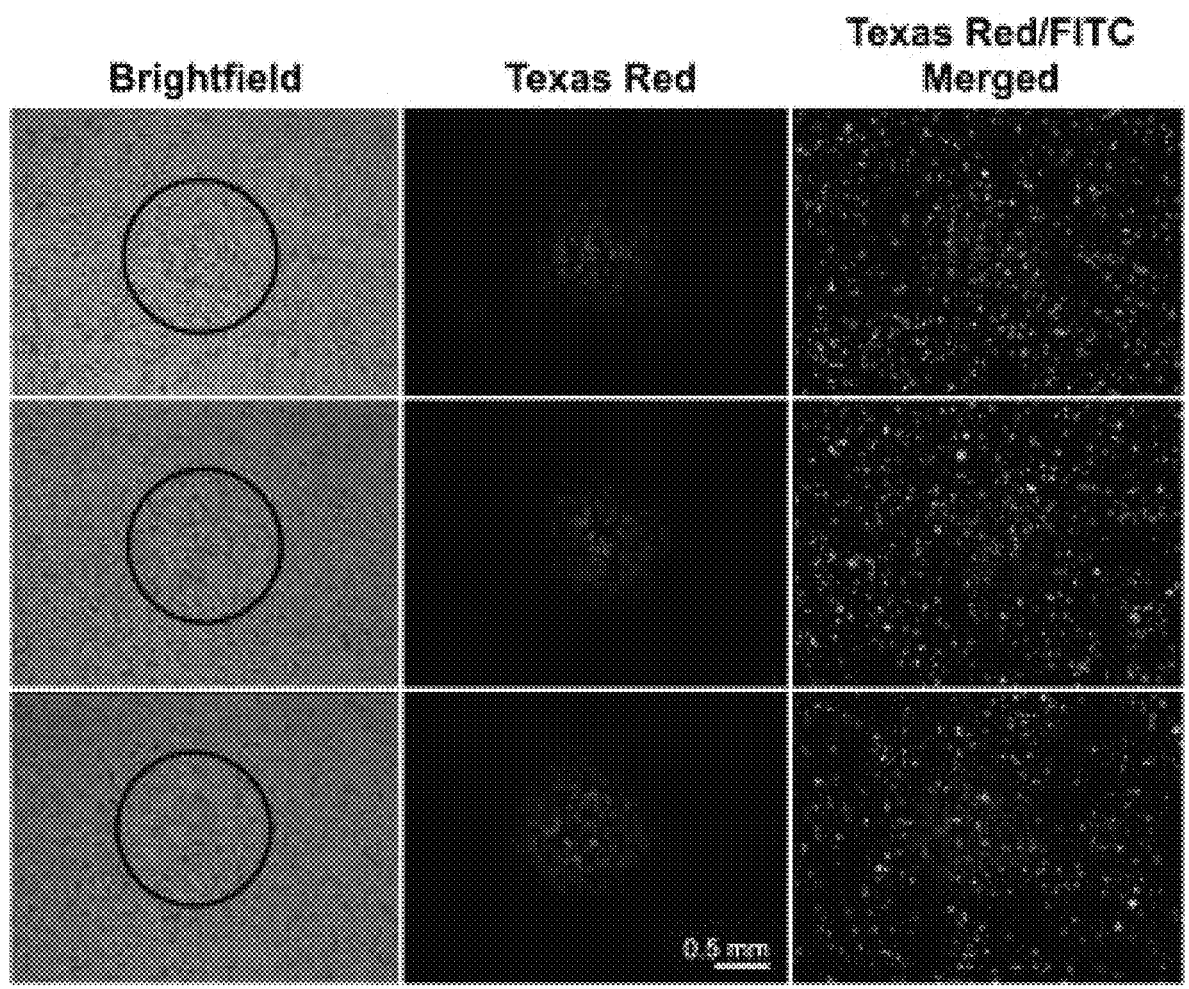
FIG. 14 shows marker-free rVACVs can be purified using the EPPIC platform. vFREE, a replication-constitutive rVACV expressing a GOI (dsRed), was generated by homologous recombination with viTetG, a tet-inducible virus expressing EGFP. vFREE was purified under light microscopy to demonstrate purification of a marker-free rVACV. Cell monolayers in 100 mm dishes were infected with infection/transfection lysate at a dilution of 10$^{-2}$, incubated for 2 days, then imaged using an inverted fluorescence microscope. Plaques were readily identified under brightfield and then confirmed to be a result of vFREE replication (dsRed$^+$). Parental viTetG was detected by EGFP expression (abortive infections).

The EPPIC platform disclosed herein utilizes reagents and equipment found in most standard virology laboratories. Nevertheless, if fluorescence microscopy is unavailable, there are alternative strategies. By way of non-limiting example this platform has been used to successfully purify rVACVs through "blind" passaging by simply transferring the supernatant of infected cells, rather than the cell lysate. In the absence of inducer, the vIND parental virus only abortively infects cells and therefore, few infectious parental VACV particles are released into the supernatant. Therefore, the vast majority of virions released into the supernatant are the rVACV. While the technique of serial passage of supernatant is technically simpler, the concentration of rVACV in the supernatant is typically low. Thus, serial passage of cell lysate results in a more reliable and therefore faster purification. In a second non-limiting example, the platform has been used to successfully purify a marker-free rVACV by relying solely on light microscopy to identify regions of cytopathic effect (a result of rVACV replication since purification is performed in the absence of parental VACV inducer; FIG. 14). Thus, even if a fluorescence microscope is unavailable, the EPPIC platform can be utilized for the rapid purification of rVACVs.

It is an object of the disclosed platform to enable generation of vIND parental viruses at multiple loci in VACV. Based on this capability the EPPIC platform can be used to rapidly generate rVACVs that contain two (or more) heterologous DNA constructs at distinct (and distant) genetic loci to express multiple genes of interest (GOIs) e.g., for multi-pathogen vaccines. Separating the genetic constructs into distant VACV loci would allow repetition of VACV promoters or other genetic elements, or incorporation of multiple similar antigens (e.g., glycoproteins of related viruses) while minimizing the risk of homologous recombination and genetic instability.

It is an object of the disclosed platform and methods to allow for the generation and purification of VACV vectors, with or without screening markers, by simple modifications to a DNA shuttle vector, thus allowing the rapid development, updating, and refinement of personalized or custom vaccines, therapeutic vectors, and vaccines for novel pathogenic agents of pandemic potential in a matter of days.

It is an object of the disclosed platform and methods to only require standard cell lines, standard cell culture media (no agarose overlay), and minimal equipment (fluorescence and/or light microscope). Exemplary cell lines include, but are not limited to, BS-C-1, COS, HEK-293, BHK, CHO, TM4, CVI, VERO-76, HELA, MDCK, BRL 3A, and/or NIH/3T3 cells.

Recombinant VACVs

The methods disclosed herein effectively and efficiently generate and purify recombinant VACVs. In some embodiments, the methods effectively and efficiently generate and purify recombinant poxviruses. In some such embodiments, the recombinant poxvirus is selected from recombinant orthopoxvirus, recombinant parapoxvirus, recombinant yatapoxvirus, recombinant molluscipoxvirus, and recombinant avipoxviruses. Exemplary recombinant poxviruses include, but are not limited to, recombinant smallpox virus, recombinant vaccinia virus, recombinant cowpox virus, recombinant monkeypox virus, recombinant rabbitpox virus, recombinant orf virus, recombinant pseudocowpox, bovine papular stomatitis virus, recombinant tanapox virus, recombinant yaba monkey tumor virus, recombinant molluscum contagiosum virus, recombinant canarypox virus, and recombinant fowlpox virus.

In some embodiments, the recombinant poxviruses comprises tet operon elements. In some embodiments, the tet operon elements comprise a tet gene (e.g., the tetR gene). In preferred embodiments, the tet gene is the tetR gene. In some embodiments, the tet operon further comprises a tet operator element ($O_2$).

In some embodiments, the recombinant poxviruses comprises lac operon elements. In some embodiments, the lac operon elements comprise a lac gene (e.g., the lacI gene). In preferred embodiments, the lac gene is the lacI gene. In some embodiments, the lac operon further comprises a lac operator element (O).

Vaccines and Medicaments

It is an object of the disclosed platform and methods to be adaptable to other poxviruses used for vaccine and therapeutic development (such as avipoxviruses and others).

Accordingly, disclosed herein are vaccines and medicaments comprising one or more of the recombinant VACVs disclosed herein, such as, for example a recombinant poxvirus. In some embodiments, disclosed herein are vaccines and medicaments comprising one or more recombinant poxviruses comprising tet operon elements. In an aspect, a vaccine or medicament comprises one or more recombinant poxviruses comprising tet operon elements, and a pharmaceutically acceptable excipient.

In some embodiments, the tet operon elements comprise a tet gene, such as, for example, tetR. In some embodiments, the tet operon further comprises a tet operator element ($O_2$).

In some embodiments, the lac operon elements comprise a lac gene, such as, for example the lacI gene. In some embodiments, the lac operon further comprises a lac operator element (O).

In some embodiments, the disclosed recombinant VACVs may be administered to a subject to elicit an immune response. For example, in some embodiments, one or more recombinant poxviruses comprising tet operon elements or lac operon elements can be administered to a subject to induce an immune response in the subject.

Administration can be done by any route of administration as determined by a skilled person. Preferably, administration is intramuscular, intravenous, subcutaneous (e.g., by scratching or injection), nasal (e.g., by inhalation) or oral.

Processes for preparing recombinant poxvirus containing compositions suitable as, e.g., vaccines or as a medicament are known to the person skilled in the art (see, for example, Joklik W. K. (1962), Virology 18: 9-18; Richter, K. H. (1970), Abhandlungen aus dem Bundesgesundheitsamt 9: 53-57). In some embodiments, the poxvirus composition is prepared in freeze-dried form. A freeze-dried product can be stored at temperatures in the range from 4° C. to 25° C.

Processes for the freeze-drying of poxviruses, vaccinia virus in particular, and virus containing compositions and solutions suitable for this purpose are known (Burke et al. (1999), Critical Reviews in Therapeutic Drug Carrier Systems 16: 1-83).

As used herein, the term "vaccinating" includes treatment and/or prevention of a pathological condition. U.S. Pat. No. 7,094,412 teaches how to use prepared poxviruses to manufacture a vaccine. The description is incorporated herein in its entirety.

The disclosed vaccines can be used to prevent or treat a pathological condition in a subject. The term encompasses both subunit vaccines, i.e., vaccine compositions containing antigens that are separate and discrete from a whole organism with which the antigen is associated in nature, as well as compositions containing the recombinant poxvirus of the present invention carrying, inter alia, the antigen and/or an epitope thereof. The vaccine may or may not include one or more additional components that enhance the immunological activity of the active component. A vaccine may additionally comprise further components typical to pharmaceutical compositions. The vaccine of the present invention is, preferably, for human and/or veterinary use.

The vaccine or the composition comprising the pox virus may generally include one or more pharmaceutically acceptable carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules, such as proteins, polysaccharides, polylactic acids, polyglycolic acids, polymeric amino acids, amino acid copolymers, lipid aggregates, or the like.

The pharmaceutical composition or vaccine according to the present invention may comprise an adjuvant. As used herein, an "adjuvant" refers to a substance that enhances, augments, or potentiates the host's immune response (antibody and/or cell-mediated) to an antigen or fragment thereof. A typical adjuvant may be aluminium salts, such as aluminium hydroxide or phosphate, Quil A, bacterial cell wall peptidoglycans, virus-like particles, polysaccharides, toll-like receptors, nano-beads, etc. (Aguilar et al. (2007), Vaccine 25: 3752-3762,).

The following are provided for exemplification purposes only and are not intended to limit the scope of the invention described in broad terms above. All references cited in this disclosure are incorporated herein by reference.

EXEMPLIFICATION

Example 1: Replication-Inducible Vaccinia Virus Vectors with Enhanced Safety In Vivo Materials and Methods Cells and Viruses Cell lines were obtained from the American Type Culture Collection (ATCC, Rockville, MD, USA). African green monkey BS-C-1 (CCL-26) and human HeLa S3 (CCL-2.2) cells were grown in Dulbecco's modified Eagle medium (D-MEM; Life Technologies, Gaithersburg, MD, USA) supplemented with 10% tetracycline-tested fetal bovine serum (Atlanta Biologicals, Flowery Branch, GA, USA), MEM vitamin solution, 200 mM L-glutamine, and MEM non-essential amino acids (Gibco, Grand Island, NY, USA). All cells were grown at 37° C. in 5% $CO_2$. The L-variant of VACV strain Western Reserve (WR) was obtained from ATCC (VR-2035) and a clone (9.2.4.8) derived by sequential plaque purification was used to generate the recombinant viruses herein (Hayasaka D, Ennis F A, Terajima M. Pathogeneses of respiratory infections with virulent and attenuated vaccinia viruses. Virol J. 2007; 4:22). High-titer stocks of VACV were obtained in HeLa S3 cells and titered in BS-C-1 cells.

Animals

Five-week-old female (BALB/cJ×C57BL/6J) normal hybrid (CB6F$_1$/J) mice (stock #100007) were purchased from Jackson Laboratory and maintained in accordance with animal care protocols approved by the Institutional Animal Care and Use Committee at the University of Connecticut (Protocol Number A16-029). All inoculations were performed under isoflurane anesthesia. Weight, clinical signs (ruffled fur, hunched posture, decreased activity), and mortality were assessed daily. Euthanasia (weight loss ≥25%) was performed by carbon dioxide overdose followed by cervical dislocation.

Construction of the VACV Transfer Vectors

The schematic representation of the VACV transfer vector backbone used for the generation of the recombinant VACVs is shown in FIG. 1. The transfer vectors were generated in multiple steps by a combination of DNA synthesis (ATUM, Newark, CA, USA), PCR cloning, and standard subcloning, using engineered restriction endonuclease sites (not shown) to facilitate construction. The gpt-EGFP fusion gene for combined gpt selection and EGFP screening was developed by DNA synthesis of the *E. coli* gpt gene (based on the sequence in plasmid pMSG, GenBank:U13860) and the EGFP gene (based on the sequence in plasmid pEGFP-1, GenBank:U55761), using a previously developed strategy (Cao J X, Upton C. gpt-gus fusion gene for selection and marker in recombinant poxviruses. Biotechniques. 1997; 22(2):276-78). The tetR gene (based on GenBank:X00694) was synthesized with an internal VACV early transcriptional termination sequence (TTTTTNT (SEQ ID NO:24)) removed from the middle of the gene (Leu codon at position 358 changed from TTA to CTT) to ensure early gene expression. The tetR and gpt-EGFP genes were placed under back-to-back $P_{E/L}$ synthetic promoters (sequence TATTTAT-ATTCCAAAAAAAAAAAATAAAATTTCAATTTT-TAACTGC AGTTAAAAATTGAAATTTTAT-TTTTTTTTTTTGGAATATAAATA (SEQ ID NO:25)) (Chakrabarti S, Sisler J R, Moss B. Compact, synthetic, vaccinia virus early/late promoter for protein expression. Biotechniques. 1997; 23(6):1094-97). The transfer vectors also contained the putative E8R or A3L promoter region or a modified $P_{11}$ late VACV promoter with a tet operator ($O_2$) (Hillen W, Berens C. Mechanisms underlying expression of Tn10 encoded tetracycline resistance. Annu Rev Microbiol. 1994; 48:345-69) placed immediately after the late transcriptional initiator element sequences, as shown in Table 1. Each cassette was surrounded by 600 bp of VACV genomic sequences to the left and to the right of the intergenic regions shown in FIG. 1 (based on GenBank:NC_006998) to direct homologous recombination and insertion of the cassettes within the appropriate genomic locations. All plasmids were sequenced after synthesis or PCR cloning to confirm sequence identity.

Generation of VACVs and Preparation of High-Titer Stocks

Recombinant VACVs were generated by standard homologous recombination after transfection of the transfer vectors with FuGENE® HD transfection reagent (Promega, Madison, WI, USA) into BS-C-1 cell monolayers infected 2 h previously with VACV WR clone 9.2.4.8 at an MOI of 0.05. Recombinant gpt-expressing VACVs were plaque purified from transfection lysates in BS-C-1 cells using selection medium (25 µg/mL mycophenolic acid, 250 g/mL xanthine, and 15 µg/mL hypoxanthine) (Falkner F G, Moss B. *Escherichia coli* gpt gene provides dominant selection for vaccinia virus open reading frame expression vectors. J Virol. 1988; 62(6):1849-54) in the presence of 1 µg/mL DOX (doxycycline hyclate ≥98% TLC, Sigma-Aldrich). EGFP$^+$ plaques were visualized under a Carl Zeiss Axio Observer D1 inverted fluorescence microscope (Oberkochen, Germany) using an XF100-2 (EGFP) filter (Omega Optical, Brattleboro, VT, USA). All VACVs were plaque purified at least four times to eliminate contamination with the parental virus. High-titer stocks were generated by infecting HeLa S3 cells with the VACVs at an MOI of 0.1 in the presence of 1 µg/mL DOX. Infected cells were harvested 4 DPI by centrifugation at 300×g for 10 min and resuspension in D-MEM without tetracyclines. Cells were then lysed by freezing and thawing, sonicated, and trypsinized. Finally, cell lysates were clarified to remove contaminating cell debris by a second round of sonication and centrifugation at 500×g for 10 min. For use in inoculation, these stocks were amplified in HeLaS3 cells, processed as described above, then pelleted through a 36% sucrose cushion (Earl P L, Moss B, Wyatt L S, Carroll M W. Generation of recombinant vaccinia viruses. Curr Protoc Mol Biol. 2001; Chapter 16:Unit 167).

Analysis of Recombinant VACV Stability and Purity

To detect any residual parental VACV after plaque purification, EGFP expression was confirmed by fluorescence microscopy. Briefly, plaque assays were performed on BS-C-1 cell monolayers in 6-well plates in the absence or presence of 1 µg/mL DOX using high-titer stocks. After 2 days of incubation at 37° C., plaques were analyzed by both brightfield and fluorescence microscopy to detect any EGFP-negative plaques that could be present and would represent unstable recombinants or recombinants needing further plaque purification. The genomic organization of each recombinant VACV around the insertion site was checked by PCR analysis of viral DNA purified using a small-scale method employing micrococcal nuclease (Lai A C, Chu Y. A rapid method for screening vaccinia virus recombinants. Biotechniques. 1991; 10(5):564-65). The primer sequences used are shown in Table 2 and their relative locations in FIGS. 1B-1D. The primer combinations used for PCR analysis included 1-3, 2-4, 3-4, 1-6, 2-5, 5-6, 1-8, 2-7, and 7-8 (FIG. 1). As a positive control for VACV DNA, primers 9 and 10 were used to amplify a region of the I8R gene.

The Effect of DOX on Plaque Formation

The ability of the VACVs to replicate in the absence or presence of inducer (DOX) was investigated by standard plaque assay. Briefly, near-confluent BS-C-1 cell monolayers in 24-well plates were infected with the VACVs at approximately 5-20 plaque-forming units (PFU)/well in the absence or presence of 1 µg/mL DOX and incubated at 37° C. for 2 or 7 days. Cells were stained and fixed with 0.5% crystal violet in 10% ethanol/20% formaldehyde and isolated viral plaques were imaged with a digital camera or an inverted microscope.

For the analysis of plaque formation by fluorescence microscopy, near-confluent BS-C-1 cell monolayers in 24-well plates were infected with the VACVs at 5-20 PFU/well in the absence or presence of 1 µg/ml DOX. Plaques and infected cells were imaged at 2, 4, 6, 8, 10, and 12 DPI. In a subset of wells infected with the VACVs in the absence of inducer, DOX was added at 2, 4, 6, 8, or 10 DPI and any plaques that formed were imaged 2 days later.

Effect of DOX on Plaque Size

The size of the plaques formed by the VACVs in the absence or presence of DOX was investigated by plaque assay. Briefly, near-confluent BS-C-1 cell monolayers in 12-well plates were infected with the VACVs at 30 PFU/well in the absence or presence of 1, 10, 100, or 1000 ng/mL DOX and incubated at 37° C. for 36 h. Cells were stained and fixed with 0.5% crystal violet in 10% ethanol/20% formaldehyde and the radius of isolated plaques was measured under an inverted microscope with measurement-capable software (AxioVision 4.8.1, Carl Zeiss).

Effect of DOX on Viral Replication In Vitro

Triplicate monolayers of near-confluent BS-C-1 cells were infected with the VACVs at an MOI of 0.01 in 24-well plates in the absence of tetracyclines. After 1 h, supernatants were aspirated and replaced with medium containing 0, 1, 10, 100, or 1000 ng/mL of DOX. Immediately after this step (to determine input titer) or after 48 h of incubation at 37° C. (to determine virus yield), cells were scraped, centrifuged, and resuspended in 0.5 mL of D-MEM. Samples were processed in three cycles of freeze/thaws and sonication, followed by trypsinization, sonication, and centrifugation for 10 min at 500×g to clarify. Virus titers were then determined by a plaque assay on BS-C-1 cells (in duplicate) in the presence of 1 µg/mL DOX.

Transient Complementation

Plasmids expressing the A6L or A3L genes under the VACV $P_{11}$ late promoter ($pP_{11}A6L$, or $pP_{11}A3L$, respectively) were generated by PCR cloning with primers 11-12 (A6L) or 13-14 (A3L) (Table 2). Primers were designed as in by Hagen C J, Titong A, Sarnoski E A, and Verardi P H (Antibiotic-dependent expression of early transcription factor subunits leads to stringent control of vaccinia virus replication. Virus research. 2014; 181:43-52). Monolayers of near-confluent BS-C-1 cells were infected with $viP_{11}A6L$ or $viP_{11}A3L$ at an MOI of 0.01 in the absence of tetracyclines in 24-well plates. After 1-hour, infected monolayers were either collected to determine input titers, or were transfected using FuGENE® HD transfection reagent with 0.5 µg plasmid expressing the A6L or A3L genes, under the control of the $P_{11}$ promoter ($pP_{11}A6L$, or $pP_{11}A3L$, respectively), or no plasmid (mock). Cells were incubated for 48 h at 37° C. in the absence or presence of 1 µg/mL DOX, then scraped, centrifuged, and resuspended in 0.5 mL of D-MEM. Virus titers were then determined by a plaque assay on BS-C-1 cells (in duplicate) in the presence of 1 µg/mL of DOX.

viP11A6L In Vivo Studies

Groups of five $CB6F_1/J$ mice were established based on average body weight over three consecutive days. Each group was formed so that mean body weight and standard deviation between groups were approximately equal. At 1 day prior to infection, DOX was filter-sterilized and diluted in autoclaved water at 2, 0.25, 0.125, 0.025, and 0.005 mg/mL, and provided ad libitum to the appropriate group (Grigg P, Titong A, Jones L A, Yilma T D, Verardi P H. Safety mechanism assisted by the repressor of tetracycline (SMART) vaccinia virus vectors for vaccines and therapeutics. Proc Natl Acad Sci USA. 2013; 110(38):15407-12). DOX water was freshly diluted and replaced every other day through Day 14. On day 0, all groups were inoculated intranasally (approximately 10 µL per naris) with approximately $5 \times 10^4$ PFU $viP_{11}A6L$ in a final volume of 20 µL sterile PBS. Weight, clinical signs, and mortality were assessed daily until 14 DPI. Animals were euthanized by $CO_2$ overdose and cervical dislocation if weight loss ≥25%.

To evaluate weight loss and survival, groups of 10 $CB6F_1/J$ mice were established, and 0.125 mg/ml DOX in drinking water was provided to appropriate groups as described above. On day 0, groups were inoculated intranasally (approximately 10 µL per naris) with a lethal dose of approximately $2 \times 10^6$ PFU virus ($viP_{11}A6L$ or WR) in a final volume of 20 L sterile PBS. Weight, clinical signs, and mortality were assessed daily until 14 DPI. Animals were euthanized by $CO_2$ overdose and cervical dislocation if weight loss ≥25%.

Replication of viP11A6L in Ovaries

To assess viral replication in ovaries, groups of five $CB6F_1/J$ mice were inoculated intraperitoneally with approximately $2 \times 10^6$ PFU $viP_{11}A6L$ or WR, in the presence or absence of DOX. On day 6 post-infection, mice were euthanized and ovaries collected for processing. Ovaries were weighed and homogenized in 10% volume D-MEM by weight. Homogenates were processed in three cycles of freeze/thaws and sonication, followed by trypsinization, sonication, and centrifugation for 10 min at 500×g to clarify. Supernatants were used to titrate virus in 6-well plates of near-confluent BS-C-1 cells in the presence of 1 µg/mL DOX.

Statistical Analyses and Image Processing

Statistical analyses were performed with GraphPad Prism v. 7.0c (GraphPad Software, La Jolla, CA, USA). Images were processed in Adobe Photoshop CS6 (Adobe Systems, San Jose, CA, USA) with no manipulations other than for contrast.

Introduction to Example 1

In this example, three VACV genes (E8R, A3L, and A6L) conserved among all chordopoxviruses (Upton C, Slack S, Hunter A L, Ehlers A, Roper R L. Poxvirus orthologous clusters: toward defining the minimum essential poxvirus genome. J Virol. 2003; 77(13):7590-600) that encode virion core proteins or a protein involved in virion morphogenesis were selected as candidate genes to generate replication-inducible VACVs. The elements of the tet operon were used to design and construct rVACVs that inducibly express the E8R, A3L, or A6L genes. The properties of these rVACVs were evaluated and characterized.

The results presented in this example show rVACVs inducibly expressing A3L, A6L, or E8R replicate indistinguishably from wild-type VACV in the presence of tetracyclines, and that rVACVs inducibly expressing A3L or A6L only abortively infect cells in the absence of antibiotics. Furthermore, a rVACV inducibly expressing A6L was not detected in mice infected in the absence of tetracyclines but caused weight loss and mortality similar to wild-type VACV in the presence of tetracyclines.

Results

Design of Tet-Responsive Late Promoters and Construction of Recombinant Viruses

Replication-inducible recombinant VACVs were designed by expressing the tetR gene under a constitutive VACV promoter and incorporating $tetO_2$ immediately downstream from the promoters directing the expression of the E8R, A3L, or A6L genes (FIG. 1A). VACV late promoter sequences contain an A/T-rich stretch of approximately 20 bp, a 6 bp spacer region, and a highly conserved TAAAT (A/G) (SEQ ID NO:1) transcriptional initiator element (Yilma T. Applications of recombinant vaccinia virus for veterinary vaccines. Dev Biol Stand. 1994; 82:201-9). The intergenic sequences upstream from the E8R and A3L genes are 124 and 52 bp, respectively. Since they are expected to contain only the promoters for the E8R and A3L genes, the O2 operator was inserted immediately after the putative late transcriptional initiator sequence (TAAATA (SEQ ID NO:2)) of these genes as shown in FIG. 1B and FIG. 1C, and in Table 1. The intergenic region upstream of the A6L gene is only 23 bp, and since it is shorter than the typical late poxvirus promoter, it is likely that a segment of the A6L promoter is located within the upstream A7L gene. The intergenic region contains more than one putative late transcriptional initiator sequence, so the promoter boundaries could not be identified with confidence. Therefore, the well-characterized F17R ($P_{11}$) late promoter, which has been used successfully as a lac-responsive promoter (Yilma T. Applications of recombinant vaccinia virus for veterinary vaccines. Dev Biol Stand. 1994; 82:201-9), was used to control the transcription of the A6L gene (FIG. 1D and Table 1). The resulting recombinant VACVs (viE8R for VACV inducible E8R, viA3L for VACV inducible A3L, and $viP_{11}A6L$ for VACV inducible A6L using the $P_{11}$ promoter) were expected to replicate only in the presence of tetracyclines such as DOX.

A series of cloning steps were used to build the transfer vectors based on existing plasmids, designed synthetic DNA sequences, and PCR cloning. The final transfer vectors contained the selectable *Escherichia coli* xanthine-guanine phosphoribosyl transferase (gpt) gene and the screening marker enhanced green fluorescent protein (EGFP) gene as a fusion gene (gpt-EGFP) under the control of the synthetic strong early/late VACV promoter $P_{E/L}$ (Chakrabarti S, Sisler J R, Moss B. Compact, synthetic, vaccinia virus early/late promoter for protein expression. Biotechniques. 1997; 23(6): 1094-7) (thus allowing both selection and screening of recombinants using a single VACV promoter), the repressor gene tetR under another (back-to-back) $P_{E/L}$ promoter, a tet-responsive promoter ($P_{E8R}O_2$, $P_{A3L}O_2$, or $P_{11}O_2$) to control the expression of the target genes, and left and right recombination sequences (the first 600 bp to the left and to the right of the intergenic regions shown in FIG. 1B-1D) to direct the precise insertion of the genetic elements contained in each cassette by homologous recombination. The recombinant viruses were successfully constructed and plaque purified in the presence of mycophenolic acid selection medium and DOX. High-titer stocks lacked EGFP⁻ plaques that would represent unstable recombinant VACVs or residual parental (wild-type) virus. In addition, PCR analysis of viral DNA purified from high-titer stocks with multiple primers spanning the regions of interest (FIG. 1B-1D and Table 2) confirmed the overall genetic organization of these regions in each recombinant VACV.

$viP_{11}A6L$ Forms Plaques in the Presence of DOX and Produces Abortive Infections in the Absence of DOX The ability of the putative inducible viruses to replicate in the absence or presence of inducer was first investigated by performing standard plaque assays in BS-C-1 cells, either in the absence or presence of DOX (1 µg/mL), followed by crystal violet staining 2- or 7-days post-infection (DPI). Isolated plaques that formed 2 DPI in the presence of DOX by viE8R, viA3L, and $viP_{11}A6L$ were typical (FIG. 2A and FIG. 2B) and identical to wild-type WR plaques in size. In the absence of DOX, viE8R and viA3L formed distinct plaques 2 DPI (FIG. 2A and FIG. 2B), suggesting that control of E8R and A3L gene expression was unsuccessful. However, no plaques could be detected 2 DPI for $viP_{11}A6L$ in the absence of DOX (FIG. 2A and FIG. 2B). Moreover, plaques were not observed in cells infected with $viP_{11}A6L$

TABLE 1

SEQUENCE OF THE PUTATIVE NATURAL PROMOTERS AND THE TET OPERATOR-CONTROLLED PROMOTERS USED TO GENERATE THE REPLICATION-INDUCIBLE VACVS.

| Promoter[a] | Sequence |
|---|---|
| F17R (P11) natural | ATTTAGAATATATGTATGTAAAAATATAGTAGAATTTCATTTTGTTTTTTCTATG CTATAAATG (SEQ ID NO: 3) |
| $P_{11}O_2$[c] | ATATAGTAGAATTTCATTTTGTTTTTTCTATGCTATAAATA TCCCTATCAGTGATAGAGACGGCCGATG (SEQ ID NO: 4) |
| E8R natural | GTATAATCCCATTCTAATACTTTAACCTGATGTATTAGCATCTTATTAG AATATTAACCTAACTAAAAGACATAACATAAAAACTCATTACATAGTTGAT AAAAAGCGGTAGGATATAAATATTATG (SEQ ID NO: 5) |
| $P_{E8R}O_2$ | GTATAATCCCATTCTAATACTTTAACCTGATGTATTAGCATCTTATTAGAATATT AACCTAACTAAAAGACATAACATAAAAACTCATTACATAGTTGATAAAAAGCGGTA GGATATAAATATCCCTATCAGTGATAGAGACGGCCGATG (SEQ ID NO: 6) |
| A3L natural | TAAGATTGGATATTAAAATCACGCTTTCGAGTAAAAACTACGAATATAAA TAATG (SEQ ID NO: 7) |
| $P_{A3L}O_2$ | TAAGATTGGATATTAAAATCACGCTTTCGAGTAAAAACTACGAATATAAATATCCC TATCAGTGATAGAGACGGCCGATG (SEQ ID NO: 8) |
| A6L natural | ACAACTAAATCTGTAAATAAATAATG (SEQ ID NO: 9) |

[a]The putative natural promoters were defined as the intergenic regions upstream from the genes. The O2-controlled promoters are based on the putative natural promoters or the F17R (P11) promoter.
[b]The promoter sequences are shown with the putative late transcriptional initiator element sequences boxed, the start codons bolded, and the O₂ operator sequences underlined.
[c]The $P_{11}O_2$ promoter was used to control expression of E8R in viP11E8R, A3L in $viP_{11}A3L$, and A6L in $viP_{11}A6L$.

in the absence of DOX even 7 DPI (FIG. 2A), when the entire cell monolayer infected with WR, viE8R, or viA3L displayed extensive cytopathic effects (CPE) and therefore destruction of the monolayer, resulting in a lack of crystal violet staining.

Plaque formation in BS-C-1 cells was also investigated in unfixed cells by brightfield and fluorescence microscopy. Under fluorescence microscopy, viE8R and viA3L formed typical plaques both in the absence and presence of DOX. However, with $viP_{11}A6L$, only single EGFP$^+$ cells could be detected in the absence of DOX (FIG. 2C). The frequency of these cells corresponded roughly to the number of plaques obtained in the presence of DOX, where EGFP plaques were observed (FIG. 2D). Under high magnification, the single EGFP$^+$ cells appeared normal and there was no evidence of EGFP expression in the neighboring cells (FIG. 2C). Taken together, these observations are indicative of abortive infections. In addition, detection of high levels of EGFP expression in these abortively-infected cells suggests that late gene expression from the $P_{E/L}$ promoter was not compromised in the absence of DOX. When DOX was added to these abortively-infected cells 2, 4, or 6 DPI, replication resumed and plaques were visible 2 days later (FIG. 2D), indicating that transcription of the A6L gene was sufficient to allow the resumption and completion of the replication cycle. However, plaques were not detected when DOX was added 8 or 10 DPI, demonstrating that resumption and completion of the replication cycle was only allowed up to 6 DPI.

$viP_{11}A6L$ did not form plaques. In the presence of 10, 100, and 1000 ng/ml DOX, $viP_{11}A6L$ formed typical plaques that were indistinguishable from plaques formed by WR.

The replication of each inducible virus was assessed in BS-C-1 cells infected at a multiplicity of infection (MOI) of 0.01 in the absence or presence of multiple concentrations of DOX by determining virus yield 48 hpi. As expected, the wild-type WR strain replicated equally in the absence or presence of DOX (FIG. 3B). Additionally, viE8R and viA3L replicated indistinguishably from WR both in the absence and presence of DOX. $viP_{11}A6L$ yield was below the input level at 0 and 1 ng/mL of DOX. More importantly, $viP_{11}A6L$ yield at ≥10 ng/ml of DOX was indistinguishable from WR, demonstrating that $viP_{11}A6L$ replicates to wild-type levels under these conditions.

VACV Expressing a #L Under the $P_{11}$ Promoter is Replication-Inducible and Replicates Indistinguishably from Wild-Type VACV in the Presence of DOX The putative natural promoter sequences present in the upstream intergenic regions were used to control the expression of the E8R and A3L genes in viE8R and viA3L, respectively (FIG. 1 and Table 1). Since viE8R and viA3L replicated even in the absence of tetracyclines, indicating a lack of control of E8R or A3L gene expression, respectively, the natural promoters of the A3L and E8R genes were replaced with the inducible late $P_{11}O_2$ promoter used to develop $viP_{11}A6L$ (Table 1). This was accomplished by replacing the $P_{E8R}O_2$ and $P_{A3L}O_2$ promoters in the transfer

TABLE 2

PRIMERS USED TO AMPLIFY WILD-TYPE AND RECOMBINANT VACV GENOMIC REGIONS.

| Primer | Gene | Sequence (5' to 3') |
|---|---|---|
| 1 | tetR | GACGCCTTAGCCATTGAGAT (SEQ ID NO: 10) |
| 2 | EGFP | ACAACCACTACCTGAGCACC (SEQ ID NO: 11) |
| 3 | E7R | TCTCCGCACATGGAACTCAT (SEQ ID NO: 12) |
| 4 | E8R | CAGAGAACGATCCATTAGCA (SEQ ID NO: 13) |
| 5 | A3L | GATGCTACTICGTCGATGGA (SEQ ID NO: 14) |
| 6 | A4L | CAAATCCAGGAGCAGCATCT (SEQ ID NO: 15) |
| 7 | A6L | TATCAACATCTGATGCGCT (SEQ ID NO: 16) |
| 8 | A7L | ATGTTATTGCGTCTGATGCC (SEQ ID NO: 17) |
| 9 | I8R (forward) | ATTTTCCAATTCCGTAGGTAAACGA (SEQ ID NO: 18) |
| 10 | I8R (reverse) | TGATCATGCTCATGAACTTCGTCTA (SEQ ID NO: 19) |
| 11 | A6L (forward) | TAAATACGGCCGATGGACAAACTTAG (SEQ ID NO: 20) |
| 12 | A6L (reverse) | ACGATAGCTAGCTTAGAATTTATACG (SEQ ID NO: 21) |
| 13 | A6L (reverse) | TAAATACGGCCGATGGAAGCCGTG (SEQ ID NO: 22) |
| 14 | A3L (reverse) | CATAATGCTAGCCTAAAATAGTTC (SEQ ID NO: 23) | viP11A6L Plaque Size and Replication are Indistinguishable from WR in the Presence of DOX The size of the plaques formed by WR and the inducible viruses in the absence or presence of multiple concentrations of DOX was analyzed by plaque assay in BS-C-1 cells. The radius of plaques formed by WR was not affected by the presence of DOX, and viE8R and viA3L formed plaques comparable in size to WR, even in the absence of DOX (FIG. 3A). In the absence or presence of 1 ng/ml DOX, vectors (FIG. 1B and FIG. 1C) with the $P_1O_2$ promoter sequence (Table 1). New recombinant VACVs were generated expressing E8R ($viP_{11}E8R$) or A3L ($viP_{11}A3L$) under $P_{11}O_2$.

Both $viP_{11}E8R$ and $viP_{11}A3L$ produced plaques like WR in the presence of DOX (FIG. 4A and FIG. 4B). In the absence of DOX, no plaques were detected with $viP_{11}A3L$ at 2 or 7 DPI, while $viP_{11}E8R$ formed noticeably smaller plaques 2 DPI and caused additional CPE by 7 DPI (FIG. 4A and FIG. 4B). Under fluorescence microscopy, viP$_{11}$E8R formed small plaques in the absence of tetracyclines and typical plaques in the presence of DOX (FIG. 4C). However, only single EGFP$^+$ cells could be detected in the absence of DOX with viP$_{11}$A3L (FIG. 4D). Under high magnification, the single EGFP$^+$ cells appeared normal and there was no evidence of EGFP expression in the neighboring cells (FIG. 4D), indicating abortive infections. When DOX was added to these abortively-infected cells 2, 4, or 6 DPI, replication was allowed to resume and plaques were visible 2 days later (FIG. 4E shows results for addition of DOX 48 h post-infection). However, as seen with viP$_{11}$A6L, viP$_{11}$A3L plaques were not detected when DOX was added 8 or 10 DPI.

The size of plaques formed by viP$_{11}$E8R and viP$_{11}$A3L was assessed by standard plaque assay in BS-C-1 cells in the absence or presence of multiple concentrations of DOX. In the presence of ≥1 ng/ml DOX, viP$_{11}$E8R formed typical plaques that were comparable to WR (FIG. 5A). However, viP$_{11}$E8R formed plaques even in the absence of DOX, although they were significantly smaller than WR plaques. No plaques were detected in viP$_{11}$A3L-infected cell monolayers in the absence or presence of 1 ng/ml DOX. In the presence of 10 ng/mL DOX, viP$_{11}$A3L formed plaques that were smaller when compared to WR. Notably, viP$_{11}$A3L produced plaques comparable in size to WR in the presence of 100 ng/ml DOX.

The replication of viP$_{11}$E8R and viP$_{11}$A3L was assessed in BS-C-1 cells infected with the VACVs at an MOI of 0.01 in the absence or presence of multiple concentrations of DOX (FIG. 5B). As expected, viP$_{11}$E8R replicated only minimally in the absence of tetracyclines, and in a dose-dependent manner when DOX was added, reaching wild-type levels at 100 ng/mL DOX. There was no evidence of viP$_{11}$A3L replication in the absence of DOX, although some level of replication was detected at 1 ng/ml, despite the fact that no plaques were observed at this concentration (FIG. 5A and FIG. 5B). At 10 ng/ml DOX, viP$_{11}$A3L replicated to intermediate levels, and more importantly, the yield at 100 ng/mL DOX was indistinguishable from WR, demonstrating that viP$_{11}$A3L replicates to wild-type levels under these conditions. Interestingly, viP$_{11}$A6L required only 10 ng/ml DOX to replicate to wild-type levels (FIG. 3), perhaps because it is needed in lower amounts to allow full replication.

Transient Complementation Allows Replication of viP11A6L and viP11A3L in the Absence of DOX To confirm that replication of viP$_{11}$A6L and viP$_{11}$A3L is dependent on the expression of the A6L or A3L genes, respectively, transient complementation assays were performed in the absence of DOX. BS-C-1 cells were infected with viP$_{11}$A6L or viP$_{11}$A3L and transfected with plasmids expressing the A6L or A3L genes constitutively under the VACV Pu promoter (pP$_{11}$A6L or pP$_{11}$A3L), or no plasmid (mock). Complementation was assessed by measuring virus yield in the absence or presence of the complementing plasmids. Cells infected with viP$_{11}$A6L and transfected with pP$_{11}$A6L yielded approximately a two-log increase in virus titers when compared to cells transfected with pP$_{11}$A3L or no plasmid, although yield was not as high as virus grown in the presence of DOX expressing the A6L gene directly from the genome (FIG. 6A). Similar results were seen in cells infected with viP$_{11}$A3L in the presence of the complementing plasmid pP$_{11}$A3L (FIG. 6B).

viP11A6L replicates in vivo in the presence of DOX

Replication of viP$_{11}$A6L in vivo was also assessed since it replicated in vitro to wild-type levels at lower concentrations of DOX (FIG. 3) when compared to viP$_{11}$A3L (FIG. 5). Groups of five female CB6F$_1$/J mice were inoculated intranasally with approximately 5×10$^4$ PFU viP$_{11}$A6L, a dose expected to cause approximately 50% mortality (Hayasaka D, Ennis F A, Terajima M. Pathogeneses of respiratory infections with virulent and attenuated vaccinia viruses. Virol J. 2007; 4:22). Mice were given either normal drinking water (NO DOX), or DOX dissolved in drinking water at either 0.005, 0.025, 0.125, 0.25, or 2 mg/mL, offered ad libitum beginning 1 day before inoculation and continued through the end of the study. Two mg/mL DOX were previously administered in drinking water to successfully induce expression from the P$_{11}$O$_2$ promoter in vivo (Grigg P, Titong A, Jones L A, Yilma T D, Verardi P H. Safety mechanism assisted by the repressor of tetracycline (SMART) vaccinia virus vectors for vaccines and therapeutics. Proc Natl Acad Sci USA. 2013; 110(38):15407-12) and wanted to determine if lower concentrations of DOX would also result in viral replication sufficient to cause weight loss and mortality like 2 mg/mL. Infected animals were weighed daily and euthanized if weight loss was ≥25%. All animals given normal drinking water (NO DOX) or 0.005 mg/mL DOX did not lose weight or display any other clinical signs, and survived with significantly higher mean group weights compared to all other groups 4-12 DPI (FIG. 7A, B). Infected animals given 0.025 mg/mL DOX lost weight but survived, with mild clinical signs such as ruffled fur. In contrast, all infected animals given ≥0.125 mg/mL DOX lost weight and displayed clinical signs including ruffled fur, hunched posture, and decreased activity. Some (12/25) succumbed to infection or were euthanized (weight loss ≥25%). Survival was significantly different when comparing NO DOX, 0.005, and 0.025 mg/mL DOX with all other groups, whereas it was not significantly different between 0.125, 0.25, and 2 mg/mL. A concentration of 0.125 mg/mL DOX was used in subsequent mouse studies because it was the lowest concentration tested that resulted in weight loss and mortality like 2 mg/mL DOX.

viP11A6L Causes Weight Loss and Mortality Similar to Wild-Type Vacv in Mice Treated with DOX To compare replication of the inducible viP$_{11}$A6L to the wild-type parental WR, groups of 10 CB6F$_1$/J mice were infected intranasally with a lethal dose of approximately 2×10$^6$ PFU virus (approximately 40 times the 50% lethal dose) (Hayasaka D, Ennis F A, Terajima M. Pathogeneses of respiratory infections with virulent and attenuated vaccinia viruses. Virol J. 2007; 4:22) in the absence or presence of 0.125 mg/ml DOX in drinking water. In the absence of DOX, all mice inoculated with viP$_{11}$A6L survived infection without weight loss or other clinical signs, with significantly higher mean weights than all other groups from 2-8 DPI. In the presence of DOX, viP$_{11}$A6L-infected mice exhibited weight loss, clinical symptoms (including ruffled fur, hunched posture, and decreased activity), and mortality indistinguishable from WR (FIG. 8A, B).

viP11A6L Viral Loads in Ovaries are Equivalent to WR Levels in the Presence of DOX and Undetectable in the Absence of DOX To compare disseminated replication of the inducible viP$_{11}$A6L to the parental WR in tissue, groups of five CB6F$_1$/J female mice were infected intraperitoneally with approximately 2×10$^6$ PFU viP$_{11}$A6L or WR, in the absence or presence of 0.125 mg/ml DOX in drinking water. Viral loads in ovaries were determined by plaque assay 6 DPI (FIG. 9), since VACV replicates to high titers in ovaries after intraperitoneal inoculation (Legrand F A, Verardi P H, Jones L A, Chan K S, Peng Y, Yilma T D. Induction of potent humoral and cellmediated immune responses by attenuated vaccinia virus vectors with deleted serpin genes. J Virol. 2004; 78(6):2770-79). Virus was not detected in ovaries from mice infected with $viP_{11}A6L$ in the absence of DOX. Conversely, viral loads in ovaries of mice infected with $viP_{11}A6L$ in the presence of DOX were indistinguishable from those of mice infected with WR.

Discussion

VACV was first used as a live vaccine to successfully eradicate smallpox worldwide (Wehrle P F. A reality in our time-certification of the global eradication of smallpox. J Infect Dis. 1980; 142(4):636-38). Since then, VACV has been used for the development of recombinant live vaccines due to the ease of genetically manipulating its large dsDNA genome while retaining infectivity, its heat stability, and relatively low cost of production (Moss B. Genetically engineered poxviruses for recombinant gene expression, vaccination, and safety. Proc Natl Acad Sci USA. 1996; 93(21):11341-48). Successful examples include a recombinant VACV expressing the rabies virus glycoprotein (V-RG) that has been used in Europe and North America against sylvatic rabies (Maki J, Guiot A L, Aubert M, Brochier B, Cliquet F, Hanlon C A, et al. Oral vaccination of wildlife using a vaccinia-rabies-glycoprotein recombinant virus vaccine (RABORAL V-RG((R))): a global review. Vet Res. 2017; 48(1):57), and a VACV expressing rinderpest virus glycoproteins provided long-term sterilizing immunity in cattle (Verardi P H, Aziz F H, Ahmad S, Jones L A, Beyene B, Ngotho R N, et al. Long-term sterilizing immunity to rinderpest in cattle vaccinated with a recombinant vaccinia virus expressing high levels of the fusion and hemagglutinin glycoproteins. J Virol. 2002; 76(2):484-91). Currently, a number of clinical trials are underway for animal and human vaccines, immunotherapies, and oncolytic therapies based on replication-competent VACV vectors (Verardi P H, Titong A, Hagen C J. A vaccinia virus renaissance: new vaccine and immunotherapeutic uses after smallpox eradication. Hum Vaccin Immunother. 2012; 8(7):961-70). However, the potential for severe adverse reactions is a concern, especially in individuals with predisposing conditions. Replication-deficient VACVs such as MVA address these safety issues, although they are not as immunogenic as replication-competent VACVs (Hatch G J, Graham V A, Bewley K R, Tree J A, Dennis M, Taylor I, et al. Assessment of the protective effect of Imvamune and Acam2000 vaccines against aerosolized monkeypox virus in cynomolgus macaques. J Virol. 2013; 87(14):7805-15), grow to lower titers in cell culture (Drexler I, Heller K, Wahren B, Erfle V, Sutter G. Highly attenuated modified vaccinia virus Ankara replicates in baby hamster kidney cells, a potential host for virus propagation, but not in various human transformed and primary cells. J Gen Virol. 1998; 79 (Pt 2):347-52) and cannot be used for oncolytic therapies. Here, we generated replication-inducible VACVs using elements of the tet operon to allow tight control of viral replication with tetracycline antibiotics. Importantly, these VACV vectors replicate at wild-type levels in the presence of inducer, and thus are expected to maintain their full immunogenic and oncolytic potential.

The replication-inducible VACVs were designed to control the expression of genes encoding core or virion morphogenesis proteins. The 02 operator sequence was placed immediately downstream from the late transcriptional initiator elements of the E8R and A3L promoters in viE8R and viA3L, respectively. In $viP_{11}A6L$, a late $P_{11}$ promoter and 02 operator sequence were used to control A6L gene expression since the natural promoter could not be identified with confidence. In addition, the tetR gene was constitutively expressed at high levels in all viruses using a synthetic early/late VACV promoter ($P_{E/L}$).

It was shown that viP11A6L does not form plaques in the absence of DOX, even when cells were incubated for 7 days. Singly-infected cells could be detected by expression of the EGFP reporter protein 2 DPI, and the neighboring cells did not show any evidence of infection such as CPE or EGFP expression. High levels of EGFP expression in these abortively-infected cells suggest that gene expression from the PE/L promoter was not compromised in the absence of DOX. In the presence of DOX, viP11A6L formed typical plaques, even when DOX was added 2, 4, or 6 DPI, indicating that the virus growth cycle resumed once A6L gene expression was allowed. Replication did not resume when DOX was added 8 or 10 DPI, possibly because the abortively-infected cells or the virus life cycle were compromised this late after infection. Additionally, viP11A6L did not form plaques in the absence or presence of 1 ng/mL DOX, and plaque sizes were indistinguishable from wild-type VACV at ≥10 ng/ml DOX. viP11A6L replicated minimally at 1 ng/mL and virus yield at ≥10 ng/ml DOX was indistinguishable from WR, demonstrating that viP11A6L replicates to wild-type levels under these conditions.

Since viE8R and viA3L replicated even in the absence of tetracyclines, it is possible that control of the native E8R and A3L promoters was unsuccessful because their sequences were not identified correctly. Thus, the putative natural E8R and A3L promoter sequences were replaced with the P11 (F17R) promoter sequence, used successfully in viP11A6L, to generate viP11E8R and viP11A3L. However, in the absence of tetracyclines viP11E8R still formed plaques (although noticeably smaller) and showed evidence of replication. Conversely, no plaques were detected in viP11A3L-infected cell monolayers in the absence or presence of 1 ng/mL DOX, and plaques comparable in size to WR were formed in the presence of 100 ng/mL DOX. Notably, there was no evidence of viP11A3L replication in the absence of DOX, and virus yield at 100 ng/mL DOX was indistinguishable from WR. Additionally, transient complementation confirmed that inducible replication of viP11A3L and viP11A6L was achieved through control of A3 and A6 expression. viP11A6L was further tested in vivo, where weight loss and mortality were observed after intranasal infection in the presence of only 0.125 mg/mL DOX in drinking water. Importantly, mice inoculated with viP11A6L in the presence of DOX exhibited similar levels of weight loss, mortality, and viral replication as mice inoculated with wild-type (WR) VACV, but did not result in any clinical signs in the absence of DOX.

The E8R gene has been studied extensively, although its specific function remains unclear (Tolonen N, Doglio L, Schleich S, Krijnse Locker J. Vaccinia virus DNA replication occurs in endoplasmic reticulum-enclosed cytoplasmic mini-nuclei. Mol Biol Cell. 2001; 12(7):2031-46; Doglio L, De Marco A, Schleich S, Roos N, Krijnse Locker J. The Vaccinia virus E8R gene product: a viral membrane protein that is made early in infection and packaged into the virions' core. J Virol. 2002; 76(19):9773-86; Kato S E, Condit R C, Moussatche N. The vaccinia virus E8R gene product is required for formation of transcriptionally active virions. Virology. 2007; 367(2):398-412). Herein, when the E8R gene was placed under the control of tet operon elements, the virus replicated both in the absence and presence of tetracyclines. Interestingly, viP11E8R plaques formed in the absence of inducer were significantly smaller than wild-type VACV plaques. Without being bound by theory, this suggests leaky expression of E8R in the absence of tetracyclines, or that the E8R gene is not essential for viral replication in vitro.

The function of A3 has been studied previously using temperature-sensitive mutants where it was found that virions formed at non-permissive temperatures were abnormal in shape, had substantially reduced infectivity, and reached transcription levels less than 2% of the wild-type virus, thus indicating A3 plays a critical role in virion morphogenesis (Kato S E, Strahl A L, Moussatche N, Condit R C. Temperature-sensitive mutants in the vaccinia virus 4b virion structural protein assemble malformed, transcriptionally inactive intracellular mature virions. Virology. 2004; 330 (1):127-46). Additionally, an inducible A3L virus has been generated using lac operon elements in a system where the bacteriophage T7 RNA polymerase is expressed under a late promoter controlled by a lac operator, and the A3L gene is placed under a T7 promoter also controlled by a lac operator (Jesus D M, Moussatche N, McFadden B B, Nielsen C P, D'Costa S M, Condit R C. Vaccinia virus protein A3 is required for the production of normal immature virions and for the encapsidation of the nucleocapsid protein L4. Virology. 2015; 481:1-12). In the presence of inducer (IPTG) the virus formed significantly smaller plaques, and in the absence of inducer, abnormal immature virions accumulated within the cytoplasm and no plaques were observed, demonstrating that A3 is required for normal virion formation. Herein, it was also successfully demonstrated that A3 is essential for VACV viral replication, and that when A3L gene expression is repressed in the absence of tetracyclines, there is no evidence of a productive infection up to 7 DPI.

The function of A6 has been previously studied in VACVs with epitope-tagged A6 and temperature-sensitive mutants (Meng X, Embry A, Sochia D, Xiang Y. Vaccinia virus A6L encodes a virion core protein required for formation of mature virion. J Virol. 2007; 81(3):1433-43), as well as IPTG-inducible viruses generated using lac operon elements (Meng X, Embry A, Rose L, Yan B, Xu C, Xiang Y. Vaccinia virus A6 is essential for virion membrane biogenesis and localization of virion membrane proteins to sites of virion assembly. J Virol. 2012; 86 (10):5603-13; Wu X, Meng X, Yan B, Rose L, Deng J, Xiang Y. Vaccinia virus virion membrane biogenesis protein A11 associates with viral membranes in a manner that requires the expression of another membrane biogenesis protein, A6. J Virol. 2012; 86(20):11276-86). These studies have shown that A6 is a late gene product packaged into the virion core, is essential for virion membrane synthesis, and plays a role in the localization of virion membranes to viral factories (Meng X, Embry A, Sochia D, Xiang Y. Vaccinia virus A6L encodes a virion core protein required for formation of mature virion. J Virol. 2007; 81(3):1433-43; Wu X, Meng X, Yan B, Rose L, Deng J, Xiang Y. Vaccinia virus virion membrane biogenesis protein A11 associates with viral membranes in a manner that requires the expression of another membrane biogenesis protein, A6. J Virol. 2012; 86(20):11276-86). The lac operon-based virus expressing A6L was shown to replicate only in the presence of IPTG, although about 10-fold less efficiently than the parental virus (Meng X, Embry A, Rose L, Yan B, Xu C, Xiang Y. Vaccinia virus A6 is essential for virion membrane biogenesis and localization of virion membrane proteins to sites of virion assembly. J Virol. 2012; 86 (10):5603-13). Herein, viP11A6L was able to replicate indistinguishably from wild-type VACV in the presence of DOX both in vitro and in vivo, suggesting that the present genetic modifications did not attenuate the virus.

Looking forward, the safety of replication-inducible vectors can be confirmed in immunocompromised or other more rigorous immunodeficient (e.g., SCID) mouse models by evaluating weight loss, clinical signs, mortality, and replication in the presence of DOX. In addition, the immunogenicity of the inducible vectors can be compared to wild-type and parental viruses to make sure that they remain fully immunogenic, and therefore maintain their vaccine and therapeutic efficacy, even under antibiotic treatment. Further modifications to the vectors (i.e., inactivation/deletion of the thymidine kinase and vaccinia growth factor genes) would enhance their use as oncolytic viruses. Finally, marker-free versions of these replication-inducible vectors (i.e., without expression of gpt and EGFP) could be developed by transient dominant selection or other methods (Falkner F G, Moss B. Transient dominant selection of recombinant vaccinia viruses. J Virol. 1990; 64 (6):3108-11). In fact, a new method was developed that can produce replication-inducible vectors that are free of screening and selectable markers and express multiple genes of interest, in as little as one week (Jasperse B, O'Connell C M, Wang Y, Verardi P H. EPPIC (Efficient Purification by Parental Inducer Constraint) Platform for Rapid Generation of Recombinant Vaccinia Viruses. Mol Ther Methods Clin Dev. 2020; 17:731-38).

Conclusions

Replication-competent VACVs induce strong, long-lived humoral and cell-mediated immune responses and are effective oncolytic viruses (Verardi P H, Titong A, Hagen C J. A vaccinia virus renaissance: new vaccine and immunotherapeutic uses after smallpox eradication. Hum Vaccin Immunother. 2012; 8(7):961-70). Thus, VACVs that depend on tetracyclines for replication can be used as safer vectors for the development of live recombinant vaccines, oncolytic therapies, and even next-generation smallpox vaccines, provided that future studies confirm immunogenicity is comparable to wild-type virus. Herein, it is shown that elements of the tet operon can be used to generate VACVs inducibly expressing the A3 or A6 virion proteins that replicate in vitro indistinguishably from wild-type VACV in the presence of tetracyclines, but only abortively infect cells in the absence of antibiotics. Similarly, a VACV inducibly expressing A6L replicated in mice at the same level as wild-type VACV in the presence of tetracyclines but was not detected in the absence of antibiotics. These replication-inducible VACVs have the potential to be used for the development of safer, next-generation recombinant live vaccines. Specifically, in the event an individual experiences an adverse reaction after vaccination due to uncontrolled viral replication, the simple cessation of tetracycline treatment should prevent further viral replication and progression of the complication. Recent cases of post-vaccinial encephalitis and progressive vaccinia in military personnel vaccinated in preparation for deployment overseas (Van Dam C N, Syed S, Eron J J, Ostrander M, Engler R J, Damon I, et al. Severe postvaccinia encephalitis with acute disseminated encephalomyelitis: recovery with early intravenous immunoglobulin, highdose steroids, and vaccinia immunoglobulin. Clin Infect Dis. 2009; 48(4): e47-e49; Lederman E R, Davidson W, Groff H L, Smith S K, Warkentien T, Li Y, et al. Progressive vaccinia: case description and laboratory-guided therapy with vaccinia immune globulin, ST-246, and CMX001. J Infect Dis. 2012; 206(9):1372-85; Lindholm D A, Fisher R D, Montgomery J R, Davidson W, Yu P A, Yu Y C, et al. Preemptive Tecovirimat Use in an Active Duty Member Presenting with Acute Myeloid Leukemia after Smallpox Vaccination. Clin Infect Dis [Internet]. 2019 Apr. 9. Available from: https:// www.ncbi.nlm.nih.gov/pubmed/30959520) emphasize the benefits of a replication-inducible smallpox vaccine, as the simple withdrawal of tetracycline antibiotic treatment would likely have promoted the clearance of VACV in these individuals. Likewise, cases of adverse reactions due to inadvertent inoculation of VACV from vaccines to household, recreational, or sexual contacts (Prevention CfDCa. Secondary and tertiary transmission of vaccinia virus after sexual contact with a smallpox vaccinee-San Diego, California, 2012. MMWR Morb Mortal Wkly Rep. 2013; 62(8): 145-47; Prevention CfDCa. Household transmission of vaccinia virus from contact with a military smallpox vaccinee-Illinois and Indiana, 2007. MMWR Morb Mortal Wkly Rep. 2007; 56(19):478-81; Hughes C M, Blythe D, Li Y, Reddy R, Jordan C, Edwards C, et al. Vaccinia virus infections in martial arts gym, Maryland, USA, 2008. Emerg Infect Dis. 2011; 17(4):730-33; Webber B J, Montgomery J R, Markelz A E, Allen K C, Hunninghake J C, Ritchie S A, et al. Spread of vaccinia virus through shaving during military training, Joint Base San Antonio-Lackland, TX, June 2014. MSMR. 2014; 21(8):2-6) would have been altogether prevented in individuals not undergoing tetracycline antibiotic therapy. In addition, the present VACV vectors still express heterologous genes (i.e., EGFP) in the absence of tetracyclines, enabling their possible use as a safer, replication-defective vaccine platform. A replication-inducible Zika virus vaccine candidate has been developed that expresses Zika virus virus-like particles from VACV in the absence of tetracyclines. The present vectors could also be used for oncolytic therapies, where treatment could be temporally controlled by the administration of tetracyclines (allowing virus replication and oncolytic action) and subsequent withdrawal (stopping virus replication).

Example 2: EPPIC (Efficient Purification by Parental Inducer Constraint) Platform for Rapid Generation of Recombinant Vaccinia Viruses Materials and Methods
Cells, Viruses, and Reagents African green monkey BS-C-1 (CCL-26) cells were obtained from the American Type Culture Collection (ATCC, Rockville, MD, USA) and were grown in Dulbecco's modified Eagle's medium (DMEM; Life Technologies, Gaithersburg, MD, USA) supplemented with 10% tetracycline-tested fetal bovine serum (FBS, Atlanta Biologicals, Flowery Branch, GA, USA). All cells were grown at 37° C. in 5% $CO_2$. The L-variant of VACV strain WR was obtained from ATCC (VR-2035) and a clone (9.2.4.8) derived by sequential plaque purification (Grigg, P., Titong, A., Jones, L. A., Yilma, T. D., and Verardi, P. H. (2013). Safety mechanism assisted by the repressor of tetracycline (SMART) vaccinia virus vectors for vaccines and therapeutics. Proc. Natl. Acad. Sci. USA 110, 15407-12) was used to generate the recombinant viruses. DOX (Sigma-Aldrich, cat. #D9891, ≥98% TLC) and IPTG (Gold Biotechnology, cat. #12481C) were added to DMEM where indicated.

Generation and Characterization of Parental VACV viLacR

The lac-inducible parental virus expressing dsRed (viLacR) was generated exactly as previously described for tet-inducible VACVs (Hagen, C. J., Titong, A., Sarnoski, E. A., and Verardi, P. H. (2014). Antibiotic-depen-dent expression of early transcription factor subunits leads to stringent control of vaccinia virus replication. Virus Res. 181, 43-52; O'Connell, Caitlin M., Jasperse, Brittany, Hagen, Caitlin J., Titon, Allison, and Verardi, Paulo H. (2020). Replication-inducible vaccinia virus vectors with enhanced safety in vivo. PLoS One 15, https://doi.org/10.1371/journal.pone. 0230711), with two modifications. During construction of the shuttle vector to generate viLacR, the tetR gene and tet operator (02) sequence were replaced with a modified lacI gene (Gatti-Lafranconi, P., Dijkman, W. P., Devenish, S. R., and Hollfelder, F. (2013). A single mutation in the core domain of the lac repressor reduces leakiness. Microb. Cell Fact. 12,67) (encoding the repressor protein of the lac operon and based on GenBank: U00096), and a synthetic 22 bp lacO sequence (5'GAATTGTGAGCGCTCACA ATTC-3') (Sadler, J. R., Sasmor, H., and Betz, J. L. (1983). A perfectly symmetric lac operator binds the lac repressor very tightly. Proc. Natl. Acad. Sci. USA 80, 6785-89), respectively. The dsRed-express gene (dsRed) encoding a red fluorescent protein and the lacI gene were placed under the control of the back-to-back $P_{E/L}$ synthetic promoters (Chakrabarti, S., Sisler, J. R., and Moss, B. (1997). Compact, synthetic, vaccinia virus early/late promoter for protein expression. Biotechniques 23, 1094-97; Grigg, P., Titong, A., Jones, L. A., Yilma, T. D., and Verardi, P. H. (2013). Safety mechanism assisted by the repressor of tetracycline (SMART) vaccinia virus vectors for vaccines and therapeutics. Proc. Natl. Acad. Sci. USA 110, 15407-12). Propagation of viLacR was performed in the presence of 1 mM IPTG. To characterize viLacR, BS-C-1 cell monolayers were infected with viLacR or wild-type WR at approximately 30 PFU/well in the absence or presence of multiple concentrations of IPTG. After 2 days, cells were stained and fixed in 0.5% crystal violet/20% ethanol and the size (radius) of approximately 30 representative plaques was measured under an inverted microscope with measurement-capable software (AxioVision 4.8.1, Carl Zeiss).

viTetG Shuttle Vector Design

The viTetG shuttle vector was generated by a combination of DNA synthesis (Atum, Newark, CA) and standard subcloning, using engineered restriction endonuclease sites to facilitate assembly. The tetR gene (based on GenBank. X00694) was synthesized with an internal VACV early transcriptional termination sequence (TTTTTNT) removed from the middle of the gene (Leu codon at position 358 changed from TTA to CTT) to ensure early gene expression (Hagen, C. J., Titong, A., Sarnoski, E. A., and Verardi, P. H. (2014). Antibiotic-dependent expression of early transcription factor subunits leads to stringent control of vaccinia virus replication. Virus Res. 181, 43-52; Grigg, P., Titong, A., Jones, L. A., Yilma, T. D., and Verardi, P. H. (2013). Safety mechanism assisted by the repressor of tetracycline (SMART) vaccinia virus vectors for vaccines and therapeutics. Proc. Natl. Acad. Sci. USA 110, 15407-12; O'Connell, Caitlin M., Jasperse, Brittany, Hagen, Caitlin J., Titon, Allison, and Verardi, Paulo H. (2020). Replication-inducible vaccinia virus vectors with enhanced safety in vivo. PLoS One 15, https://doi.org/10.1371/journal. pone.0230711). The tetR and EGFP genes were placed under back-to-back $P_{E/L}$ synthetic promoters (Chakrabarti, S., Sisler, J. R., and Moss, B. (1997). Compact, synthetic, vaccinia virus early/late promoter for protein expression. Biotechniques 23, 1094-97). The shuttle vector also contained the putative VACV D6R promoter region with a $tetO_2$ (Hillen, W., and Berens, C. (1994). Mechanisms underlying expression of Tn10 encoded tetracycline resistance. Annu. Rev. Microbiol. 48, 345-69) placed immediately after the late transcriptional initiator element sequences. The cassette was surrounded by 600 bp of VACV genomic sequences (based on GenBank: NC_006998) to the left (upstream D5R gene) and to the right (D6R gene) to direct homologous recombination and insertion of the cassette into the appropriate genomic location.

The plasmid was verified after construction by restriction enzyme digestion and PCR analysis.

Generation of rVACV viTetG

To generate viTetG, BS-C-1 cells were seeded in 12-well culture plates to approximately 85%-95% confluency. Cells were washed once with DMEM and infected with parental virus (viLacR) at a multiplicity of infection (MOI) of 0.1 for 1 h. Cells were then washed once with DMEM and overlaid with DMEM containing 2.5% FBS and both 0.1 mM IPTG and 1 µg/mL DOX. The infected cells were then transfected with a shuttle vector using FuGENE® HD transfection reagent (Promega, Madison, WI, USA) in duplicate wells. Two days later, cells were observed under light and fluorescence microscopy for evidence of viLacR replication (dsRed expression and CPE) and transfection efficiency. Cells were collected by scraping the entire surface of the well with the blunt end of a micropipette tip, centrifugation to pellet the cells, and resuspension in 0.5 mL fresh media. Cell lysates were processed by a series of three freeze/thaw cycles, sonication, trypsinization, and finally centrifugation to clarify the virus suspension.

Purification of viTetG from parental viLacR

To purify viTetG from parental viLacR, we used the cell lysate collected after the initial infection/transfection to infect 100 mm cell culture dishes at various dilutions (e.g., $10^{-1}$, $10^{-2}$) in the presence of 1 µg/mL DOX (viTetG inducer) and absence of IPTG (viLacR inducer). Two days later, cells were examined with light and fluorescence microscopy for the presence of rVACV (EGFP⁺ plaques). EGFP⁺ plaques were collected using a standard micropipette, using an EVOS FL fluorescence microscope (Thermo Fisher Scientific, Waltham, MA, USA) placed inside a biosafety cabinet to facilitate simultaneous visualization and collection. The cells were collected by aspiration of approximately 50 µL of overlay media while scraping the well surface to lift off EGFP⁺ cells. The collected cells were then resuspended in 0.5 mL of fresh media, processed (series of three freeze/thaw cycles, sonication, and trypsinization), and used to infect 24-well culture plates at several dilutions (e.g., $10^{-1}$, $10^{-2}$) in the presence of 1 µg/mL DOX and absence of IPTG. Two days later, cells were observed under light and fluorescence microscopy for the presence of EGFP⁺ plaques (viTetG replication), which were then collected and processed.

Introduction to Example 2

In this example, an EPPIC (Efficient Purification by Parental Inducer Constraint) platform was developed to generate and rapidly purify rVACVs by utilizing a vIND as the parental virus. This platform uses standard cell lines, standard cell culture media (no agarose overlay), and minimal equipment (fluorescence and/or light microscope). The main objectives were to determine optimal conditions for homologous recombination and serial purification and to generate a suite of vIND parental viruses to facilitate customization of the EPPIC platform. This platform allows for the generation and purification of replication-competent or replication-inducible VACV vectors, with or without screening markers, by simple modifications to the DNA shuttle vector, thus facilitating the development, updating, and refinement of personalized or custom vaccines in a matter of days. Most importantly, rVACVs can be purified from the vIND parental virus within 1 week by simple withdrawal of inducer (i.e., inducer constraint) during serial purification. Herein, it was demonstrated that the EPPIC platform through the generation of viTetG, a vIND expressing enhanced green fluorescence protein (EGFP).

Results

Parental VIND, viLacR, Replicates Only in the Presence of IPTG

A novel platform was developed, based on vIND vectors, to generate and purify rVACVs in as little as 6 days without any specialized equipment or special cell lines. This EPPIC platform utilizes a vIND (Hagen, C. J., Titong, A., Sarnoski, E. A., and Verardi, P. H. (2014). Antibiotic-depen-dent expression of early transcription factor subunits leads to stringent control of vaccinia virus replication. Virus Res. 181, 43-52; O'Connell, Caitlin M., Jasperse, Brittany, Hagen, Caitlin J., Titon, Allison, and Verardi, Paulo H. (2020). Replication-inducible vaccinia virus vectors with enhanced safety in vivo. PLoS One 15, https://doi.org/10.1371/journal.pone. 0230711) as the parental virus for homologous recombination with a DNA shuttle vector to generate a rVACV. By incorporating elements from either the tet or lac operon, viTet (e.g., viD6R (Hagen, C. J., Titong, A., Sarnoski, E. A., and Verardi, P. H. (2014). Antibiotic-dependent expression of early transcription factor subunits leads to stringent control of vaccinia virus replication. Virus Res. 181, 43-52)) or viLac viruses were generated, respectively, that tightly regulate transcription of a gene essential to VACV replication and thereby replicate exclusively in the presence of inducer (e.g., tetracyclines or IPTG, respectively). vINDs were generated based on several essential VACV genes (Hagen, C. J., Titong, A., Sarnoski, E. A., and Verardi, P. H. (2014). Antibiotic-dependent expression of early transcription factor subunits leads to stringent control of vaccinia virus replication. Virus Res. 181, 43-52; O'Connell, Caitlin M., Jasperse, Brittany, Hagen, Caitlin J., Titon, Allison, and Verardi, Paulo H. (2020). Replication-inducible vaccinia virus vectors with enhanced safety in vivo. PLoS One 15, https://doi.org/10.1371/journal.pone. 0230711).

Figure 10:
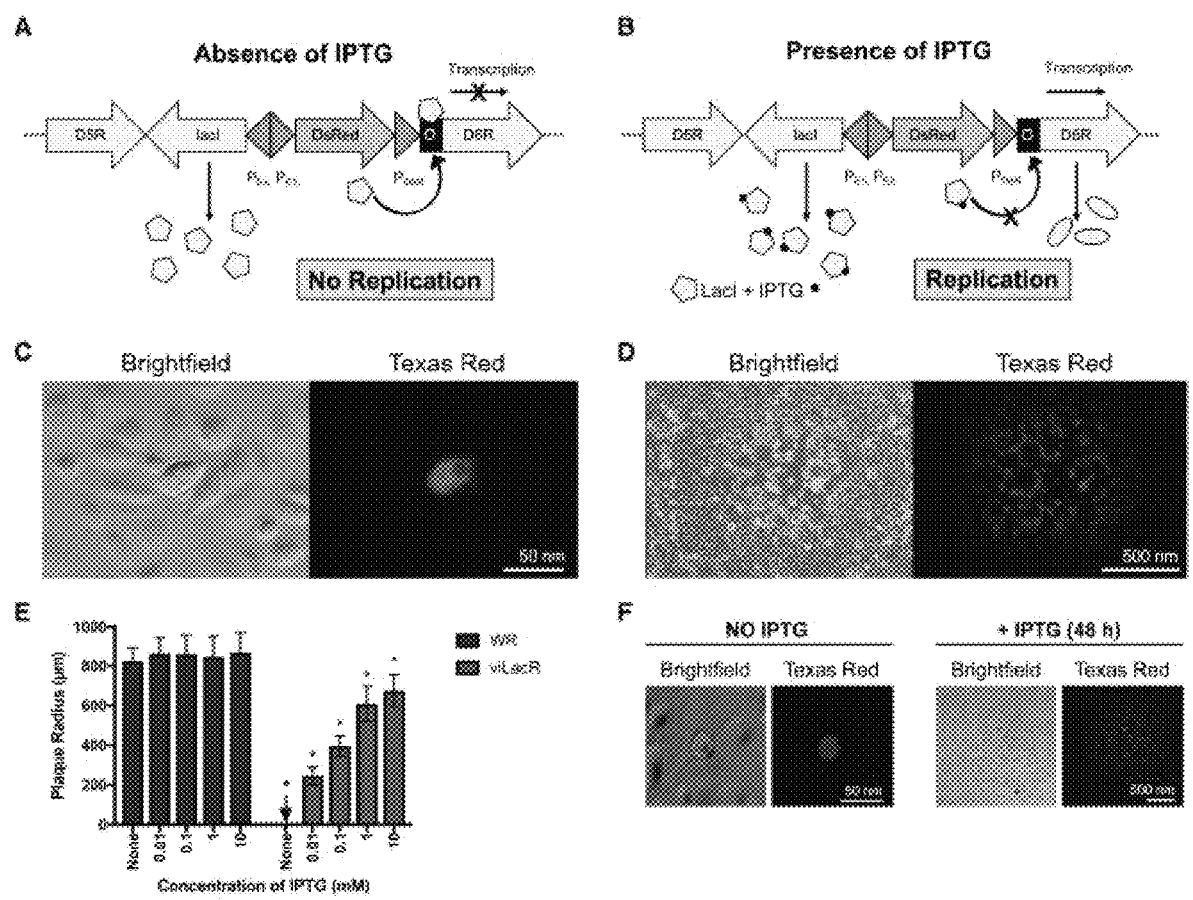
FIGS. 10A-F shows replication of viLacR, a VACV inducibly expressing the essential D6R gene, occurs only in the presence of inducer, IPTG. A cassette containing the putative D6R promoter ($P_{D6R}$) followed by the lac operator (O) sequence was inserted upstream of the D6R gene. The cassette also contained the lacI repressor gene and dsRed screening gene under back-to-back synthetic early/late VACV promoters ($P_{E/L}$).

To generate the rVACV viTetG (a vIND expressing EGFP), a lac-inducible parental virus expressing a dsRed reporter protein (viLacR) was selected. Replication of viLacR is based on the conditional expression of the essential D6R gene (encoding the small subunit of the VACV early transcription factor) (FIG. 10). In the absence of inducer (IPTG), the LacI repressor is expressed, binds the lacO operator sequence, and blocks transcription of the downstream D6R gene (FIG. 10A), thus preventing virus replication and resulting in an abortive infection (FIG. 10C), where the infected cell expresses viral-encoded genes such as the reporter dsRed gene but does not produce progeny virus (Hagen, C. J., Titong, A., Sarnoski, E. A., and Verardi, P. H. (2014). Antibiotic-dependent expression of early transcription factor subunits leads to stringent control of vaccinia virus replication. Virus Res. 181, 43-52; O'Connell, Caitlin M., Jasperse, Brittany, Hagen, Caitlin J., Titon, Allison, and Verardi, Paulo H. (2020). Replication-inducible vaccinia virus vectors with enhanced safety in vivo. PLoS One 15, https://doi.org/10.1371/journal.pone. 0230711).

However, in the presence of IPTG, LacI is expressed but binds IPTG and undergoes a conformational change and is therefore unable to bind the lacO operator sequence. Thus, transcription of the essential gene D6R occurs (FIG. 10B), and viLacR replicates freely, forming a plaque (FIG. 10D). Replication of viLacR is dependent on IPTG (FIG. 10E), with no plaques observed in the absence of IPTG, and nearly wild-type size plaques observed in the presence of at least 1 mM IPTG. Furthermore, while only single infected cells (dsRed*) can be detected 2 days post-infection (DPI) in the absence of IPTG, addition of IPTG 2 DPI results in resumption of viral replication and formation of a plaque by 4 DPI (FIG. 10F).

Figure 11:
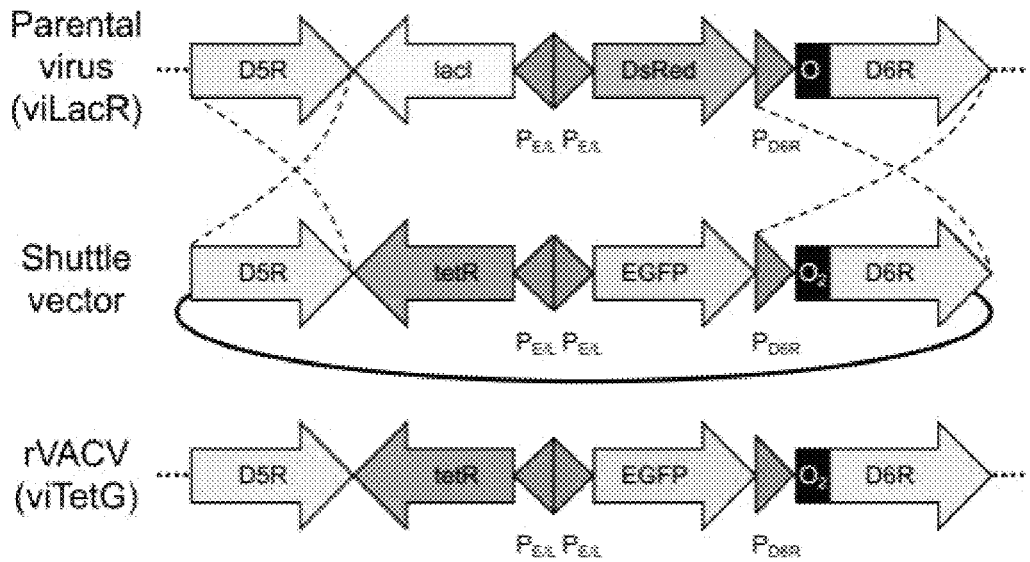
FIG. 11 shows that rVACV viTetG was generated by homologous recombination between parental viLacR and a DNA shuttle vector. viLacR (top panel) contained the D6R promoter ($P_{D6R}$) followed by the lacO sequence (O) and the lacI and dsRed genes under back-to-back synthetic $P_{E/L}$ promoters. The DNA shuttle vector (middle panel) contained the D6R gene under a tet operator ($O_2$)-controlled $P_{D6R}$ promoter and tetR and EGFP genes under back-to-back $P_{E/L}$ promoters, flanked by regions homologous to viLacR. Homologous recombination (dashed lines) between the shuttle vector (middle panel) and viLacR (top panel) generated viTetG, a tet-inducible rVACV expressing EGFP (bottom panel).

Homologous Recombination Between Shuttle Vector and Parental viLacR Generates rVACV viTetG The first step of the EPPIC platform is to design a DNA shuttle vector that contains any promoter(s) and gene(s) of interest (GOI) flanked by regions homologous to the VACV genome. The homologous regions are determined by the essential gene controlled by the inducible mechanism (right border) and its upstream gene (left border). For example, to generate viTetG (a vIND expressing EGFP), a shuttle vector was designed such that elements of the lac operon were replaced with those from the tet operon (lac replaced with tetR and lacO replaced with tetO$_2$), the GOI (EGFP) was placed under the control of a synthetic $P_{E/L}$ VACV promoter, and the entire cassette was flanked by the upstream D5R gene and the D6R essential gene (FIG. 11, middle panel). Homologous recombination between the DNA shuttle vector and parental virus viLacR generates viTetG, a tet-inducible rVACV expressing EGFP (FIG. 11).

Figure 12:
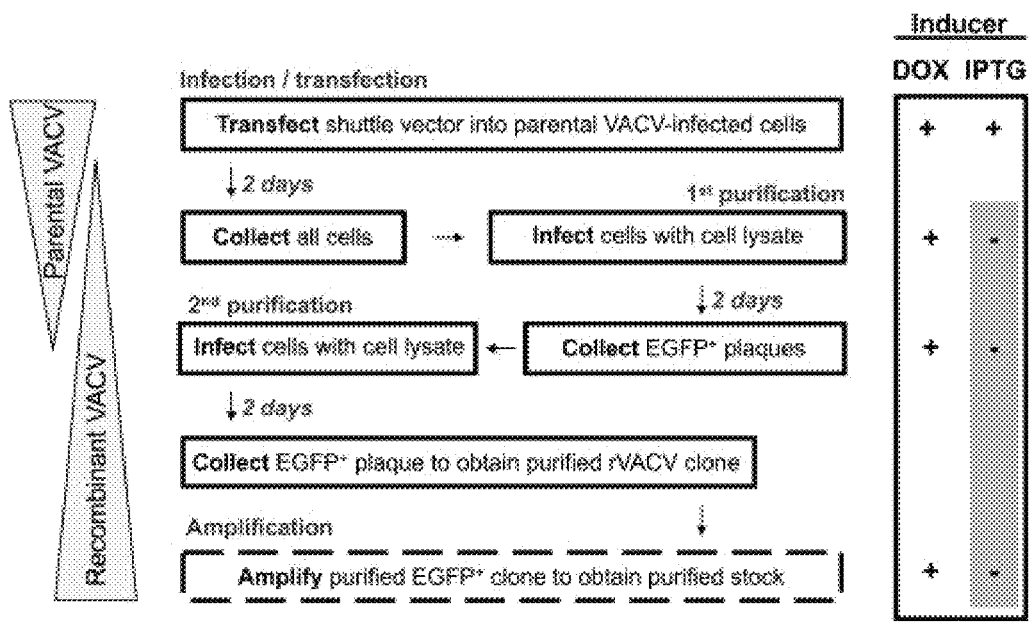
FIG. 12 shows rVACV viTetG was generated using the optimized steps of the EPPIC platform. Infection/transfection was performed at an MOI of 0.1 in the presence of viTetG inducer (DOX) and parental viLacR inducer (IPTG) and resulted in generation of viTetG by homologous recombination between a parental VACV (viLacR) and DNA shuttle vector. Purification of viTetG from viLacR was achieved by serial purification in the presence of DOX and absence of IPTG (parental inducer constraint). A purified viTetG clone was obtained within 6 days, which was then amplified to generate a working stock.

To generate viTetG, BS-C-1 cells were infected with the parental virus viLacR in the presence of parental inducer (IPTG) and rVACV inducer (tetracyclines such as doxycycline [DOX]) and subsequently transfected them with the shuttle vector (FIG. 12). Infected/transfected cells were incubated for 2 days and subsequently examined with light and fluorescence microscopy to check for cytopathic effect (CPE) and expression of fluorescence proteins (viLacR-based expression of dsRed and viTetG-based expression of EGFP). Next, the cells were collected and processed (series of three freeze/thaw cycles, sonication, and trypsinization) to obtain the intracellular virus fraction for further purification. During optimization of the EPPIC platform, it was determined that addition of parental inducer during the infection/transfection step more reliably resulted in rVACV generation. However, the addition of 0.1 mM IPTG (10-fold less parental inducer than that typically used for propagation of parental viLacR) was sufficient for rVACV generation and conveniently, should decrease the concentration of residual IPTG carried over into subsequent purifications.

rVACV viTetG was Purified from Parental viLacR in the Absence of IPTG and Presence of DOX Since viTetG should replicate only in the presence of DOX and viLacR should replicate only in the presence of IPTG, purification was performed in the presence of DOX (viTetG inducer) and absence of IPTG (viLacR inducer). During the first purification step, the processed lysate from the infection/transfection was used to infect fresh cells under "parental inducer constraint" (absence of IPTG and presence of DOX) in the absence of any special overlay (e.g., agarose) (FIG. 12). Two days later, cells were scanned under a fluorescence microscope to identify EGFP$^+$ plaques (evidence of viTetG replication). While many cells were infected by viLacR (dsRed$^+$ cells) due to the high proportion of parental virus remaining in the transfection/infection lysate, EGFP$^+$ plaques were identified. During optimization, it was determined that it was prudent to infect with several dilutions (e.g., 10$^{-1}$, 10$^{-2}$) and in a cell culture plate with a large surface area (e.g., 100 mm dish or 6-well plate) to detect the rare rVACV more easily among the abundant parental virus. Once viTetG (EGFP$^+$) plaques were identified, the plaques were simply collected with a pipet tip from the monolayer and processed (series of three freeze/thaw cycles, sonication, and trypsinization).

During the second purification step of the EPPIC platform, the cell lysate collected during the first purification step was transferred to fresh cell monolayers (several wells of a 24-well plate using dilutions of 10$^{-1}$ and 10$^{-2}$) under parental inducer constraint (presence of DOX and absence of IPTG) (FIG. 12). Any plaques that develop should be due to viTetG replication, since any residual parental viLacR should only undergo abortive infections in the absence of IPTG (FIG. 10C). Two days later, cells were examined under fluorescence microscopy. At this stage, the proportion of rVACV in the virus pool was substantially increased, such that only occasional abortive infections (due to viLacR) were detected. Individual (well-separated) viTetG (EGFP$^+$) plaques were identified, collected, and processed. In this manner, a purified clone of viTetG was obtained in only 6 days.

Figure 13:
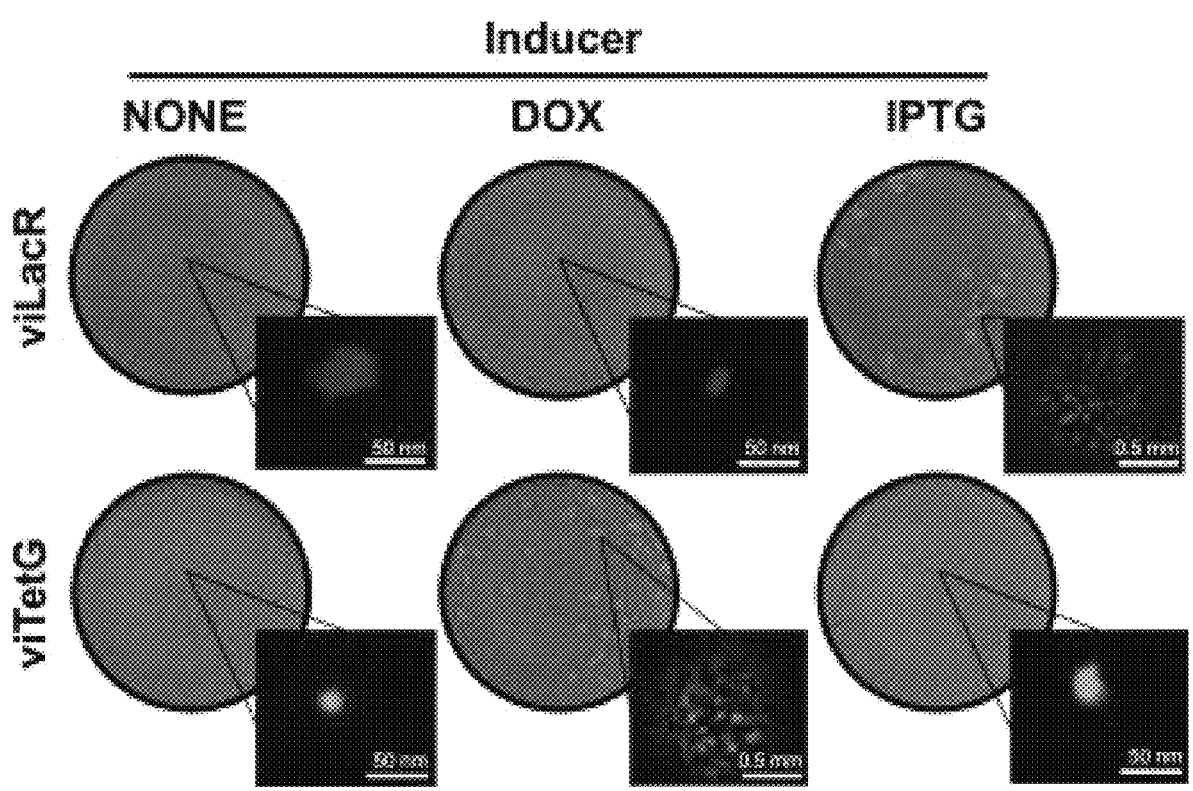
FIG. 13 shows parental virus viLACR and rVACV viTetG form plaques only in the presence of the appropriate inducer. Cells were infected with viTetG or viLacR at approximately 20 PFU/well and incubated in the absence or presence of inducer (1 μg/mL DOX or 1 mM IPTG). After 2 days, representative images were taken using an inverted fluorescence microscope. Cells were then stained and fixed in 0.5% crystal violet/20% ethanol and the entire well was imaged.

Following isolation of a purified viTetG clone, the virus was amplified further to generate a working stock (FIG. 12). To accomplish this, cell monolayers were infected with several dilutions (e.g., 10$^{-2}$, 10$^{-3}$) of the purified viTetG clone (i.e., cell lysate collected after the second purification step). Two days later, wells were observed under fluorescence microscopy to check for development of viTetG (EGFP$^+$) plaques. Wells containing a single plaque (in this case, EGFP$^+$) were examined carefully to ensure they were free of residual viLacR (i.e., dsRed$^-$) and were then incubated for several days, until the entire well exhibited CPE. At that time, the cells were collected and processed to obtain a working stock of viTetG.

viTetG Abortively Infects Cells in the Absence of DOX and Forms Plaques in the Presence of DOX Once a working stock of viTetG was obtained, the virus was characterized to ensure the correct replication phenotype (i.e., replication-inducible by DOX). Cells in 24-well culture dishes were infected with either the parental virus viLacR or rVACV viTetG at approximately 20 plaque-forming unit (PFU)/well. After 2 days, cells were imaged using a fluorescence microscope and subsequently stained and fixed with crystal violet (FIG. 13). As expected, parental virus viLacR formed dsRed$^+$ plaques only in the presence of IPTG and abortively infected cells (detected by dsRed expression) in the absence of IPTG. Furthermore, rVACV viTetG formed EGFP$^+$ plaques only in the presence of DOX and abortively infected cells (detected by EGFP expression) in the absence of DOX.

Marker-Free RVACVs can be Purified Using the EPPIC Platform

While the addition of a screening marker (e.g., dsRed or EGFP) within the rVACV makes this platform extremely straightforward, to be of maximal utility, the EPPIC platform should be customizable to purify marker-free rVACVs as well. viTetG (tet-inducible VACV expressing EGFP) were used as the parental virus to generate a marker-free replication-constitutive rVACV (vFREE) expressing a GOI (in this case, dsRed). During purification, cells were infected in the absence of DOX and were examined using light microscopy only (no fluorescence) to demonstrate the ability to purify a marker-free rVACV (i.e., relying solely on cytopathic effect). During the first purification step (FIG. 14), plaques were identified under bright field (black circles) and were secondarily confirmed to be dsRed$^+$ (expressed by vFREE and not by parental virus viTetG). vFREE plaques were readily identified by cytopathic effect and purification was continued (as in FIG. 12) to obtain a purified vFREE clone.

Figure 15:
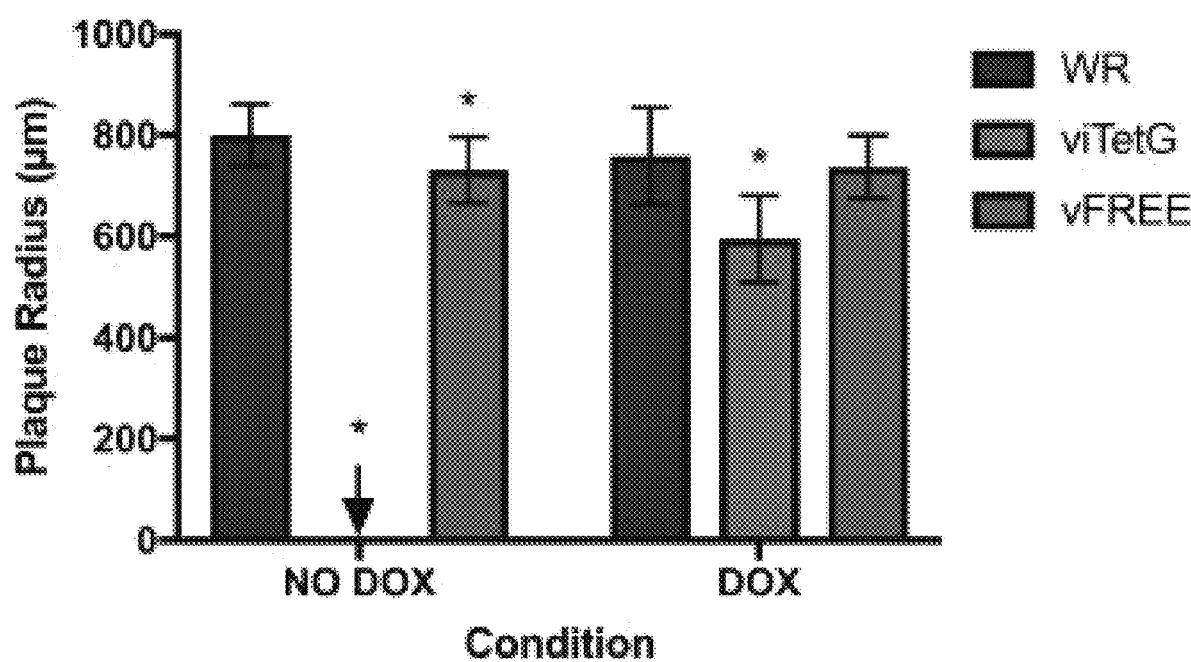
FIG. 15 shows marker-free rVACV, vFREE, forms plaques comparable to wild-type (WR) in the presence and absence of DOX, while parental VACV, viTETG, forms plaques only in the presence of DOX.

Following purification, vFREE was characterized in vitro by comparing the size of plaques formed by vFREE, wild-type VACV (Western Reserve [WR]), and the parental VACV (viTetG) in the absence or presence of 1 µg/mL DOX (FIG. 15). viTetG formed plaques only in the presence of DOX, while only abortive infections were detected in the absence of DOX. Importantly, plaques formed by vFREE were comparable to or near wild-type size in both the absence and presence of DOX. Thus, marker-free rVACVs can be readily purified using the EPPIC platform by simply using light microscopy to identify regions of cytopathic effect.

Discussion

Here, an EPPIC platform for rapid and simple purification of rVACVs in as little as 6 days is described. This platform utilizes previously generated replication-inducible VACVs (Hagen, C. J., Titong, A., Sarnoski, E. A., and Verardi, P. H. (2014). Antibiotic-dependent expression of early transcription factor subunits leads to stringent control of vaccinia virus replication. Virus Res. 181, 43-52; O'Connell, Caitlin M., Jasperse, Brittany, Hagen, Caitlin J., Titon, Allison, and Verardi, Paulo H. (2020). Replication-inducible vaccinia virus vectors with enhanced safety in vivo. PLoS One 15, https://doi.org/10.1371/journal.pone.0230711) as parental viruses that can be rapidly and efficiently removed from the parental/rVACV pool following homologous recombination by simple serial passage in the absence of parental inducer. This platform uses standard cell lines and does not require selection media, agarose overlay, or specialized equipment such as FACS. Importantly, the resulting rVACV is identical to parental with the sole exception of the precise introduction of the sequences (in the case of vFREE, the promoter $P_{11}$ and GOI dsRed) between the homologous regions.

The EPPIC platform is entirely customizable, allowing for the generation and purification of replication-competent, tet-inducible, or lac-inducible rVACVs, with or without screening markers using the purification workflow described above. To facilitate customization, we have developed a suite of viLac and viTet parental VACVs that contain the inducible mechanism at different loci within the VACV genome (e.g., D6R, A6L, F17R) with various markers (e.g., dsRed, EGFP, gusA, (Grigg, P., Titong, A., Jones, L. A., Yilma, T. D., and Verardi, P. H. (2013). Safety mechanism assisted by the repressor of tetracycline (SMART) vaccinia virus vectors for vaccines and therapeutics. Proc. Natl. Acad. Sci. USA 110, 15407-12) or lacZ). For example, to generate a lac-inducible rVACV expressing EGFP, a tet-inducible parental VACV expressing LacZ could be used and purification performed in the absence of DOX and presence of IPTG. Conversely, to generate a tet-inducible rVACV expressing LacZ, a lac-inducible parental VACV expressing dsRed could be used and purification performed in the absence of IPTG and presence of DOX. In this manner, one can simply and rapidly shuffle back and forth between viLac and viTet vectors by strategic selection of the parental virus and swapping inducer constraint during purification.

The EPPIC platform utilizes reagents and equipment found in most standard virology laboratories. Nevertheless, if fluorescence microscopy is unavailable, we have investigated alternative strategies. First, this platform was used to successfully purify rVACVs through "blind" passaging by simply transferring the supernatant of infected cells, rather than the cell lysate. In the absence of inducer, the vIND parental virus only abortively infects cells and therefore, few infectious parental VACV particles are released into the supernatant. Therefore, many virions released into the supernatant are the rVACV. While the technique of serial passage of supernatant is technically simpler, the concentration of rVACV in the supernatant is typically low. Thus, serial passage of cell lysate results in a more reliable and therefore faster purification. Second, we have successfully purified a marker-free rVACV by relying solely on light microscopy to identify regions of cytopathic effect (a result of rVACV replication since purification is performed in the absence of parental VACV inducer, FIG. 14). Thus, even if a fluorescence microscope is unavailable, the EPPIC platform can be utilized for the rapid purification of rVACVs.

Since vIND parental viruses were generated at multiple loci in VACV, the EPPIC platform can be used to rapidly generate rVACVs that contain two (or more) heterologous DNA constructs at distinct (and distant) genetic loci to express multiple GOIs (e.g., for multi-pathogen vaccines). Separating the genetic constructs into distant VACV loci would allow repetition of VACV promoters or other genetic elements, or incorporation of multiple similar antigens (e.g., glycoproteins of related viruses) while minimizing the risk of homologous recombination and genetic instability.

This novel platform enables the rapid generation and characterization of VACV vectors for a variety of applications, including standard rVACV generation for research use, rapid generation of marker-free VACV vectors for clinical use, as well as rapid characterization of vaccine antigen strategies for emerging pathogens. For example, a number of VACV-vectored vaccine candidates were generated against Zika virus by performing serial purifications for each of the candidates in parallel, to rapidly determine the best antigen strategy. Furthermore, the EPPIC platform could enable the rapid and simple generation, updating, and refining of personalized or custom VACV-vectored vaccines or therapeutic vectors in a matter of days.

The invention claimed is:

1. A method of generating recombinant poxvirus, wherein the poxvirus is vaccinia virus (VACV), and wherein a recombinant vaccina virus (rVACV) is generated expressing a gene of interest (GOI) the method comprising homologously recombining a replication-inducible VACV (vIND) parental virus genome and a DNA shuttle vector to generate the rVACVs with the GOI, wherein expression of one or more essential genes in the parental vIND is controlled by an inducible mechanism, wherein the one or more essential genes is required for viral replication of the vIND, wherein the DNA shuttle vector comprises an expression cassette comprising the gene of interest operably linked to a promoter, the cassette flanked by right and left regions that are homologous to the parental vIND virus genome, wherein the right flanking region is homologous to a region in the parental vIND genome that is upstream of the inducible mechanism and the left flanking region is homologous to a region in the parental vIND genome that is downstream of the inducible gene, such that homologous recombination between vIND and the DNA shuttle vector leads to insertion of the expression cassette into the parental vIND virus genome between the homologous regions and results in loss of the inducible mechanism control on the expression of the one or more essential genes in the rVACV, transfecting the DNA shuttle vector into parental vIND-infected cells, and purifying the rVACVs from the parental vIND by serial passage in the absence of the parental inducer.

2. The method of claim 1, wherein transfecting the DNA shuttle vector into parental vIND-infected cells is in the presence of the parental inducer.

3. The method of claim 2, wherein the rVACVs further express enhanced green fluorescence protein, and the method further comprises collecting enhanced green fluorescence protein (EGFP+) plaques between a first purification step and a second purification step, and collecting the EGFP+ plaques after a purification step to obtain purified a rVACV clone and optionally amplifying the purified rVACV clone.

4. The method of claim 1, wherein expression of the GOI is controlled by a GOI inducer such that homologous recombination renders the rVACV replication inducible, and wherein the GOI inducer is a tetracycline antibiotic or isopropyl β-D-1-thiogalactopyranoside (IPTG).

5. The method of claim 4, wherein the tetracycline antibiotic is selected from chlortetracycline, oxytetracycline, tetracycline, demethylchlortetracycline, rolitetracycline, lymecycline, clomocycline, methacycline, doxycycline, minocycline, and tertiary-butylglycylamidominocycline.

6. The method of claim 1, wherein the rVACV further comprises a screening marker selected from dsRed, EGFP, gusA, or lacZ.

7. The method of claim 1, wherein the one or more essential genes required for replication of the parental vIND is one or more of D6R, A6L, F17R, A3R, E8R.

8. The method of claim 7, wherein the parental inducer is a tet operon with a tet operator element, or a lac operon with a lac operator element.

9. The method of claim 8, wherein the lac operator element is controlled by a $P_{11}$ promoter.

* * * * *